United States Patent [19]

Hoeger et al.

[11] Patent Number: 5,580,957
[45] Date of Patent: Dec. 3, 1996

[54] GNRH ANALOGS

[75] Inventors: Carl A. Hoeger, San Marcos; Jean E. F. Rivier, La Jolla; Paula G. Theobald, Oceanside; John S. Porter, Leucadia, all of Calif.

[73] Assignee: The Salk Institute for Biological Studies, San Diego, Calif.

[21] Appl. No.: 210,619

[22] Filed: Mar. 18, 1994

Related U.S. Application Data

[63] Continuation-in-part of Ser. No. 78,965, Jun. 17, 1993, Pat. No. 5,352,796, and Ser. No. 6,729, Jan. 21, 1993, Pat. No. 5,296,468, which is a continuation-in-part of Ser. No. 669,695, Mar. 14, 1991, abandoned, which is a continuation-in-part of Ser. No. 545,239, Jun. 27, 1990, Pat. No. 5,169,932, which is a continuation-in-part of Ser. No. 428,827, Oct. 30, 1989, abandoned.

[51] Int. Cl.$^6$ ............................................. C07K 14/695
[52] U.S. Cl. ........................ 530/345; 530/313; 530/328; 530/337; 530/335; 530/334; 530/333
[58] Field of Search ............................. 530/313, 328, 530/337, 335, 334, 333, 345; 930/110; 514/15

[56] References Cited

U.S. PATENT DOCUMENTS

| | | | |
|---|---|---|---|
| 4,234,571 | 11/1980 | Nestor et al. | 514/15 |
| 4,244,946 | 1/1981 | Rivier et al. | 424/177 |
| 4,261,887 | 4/1981 | Amoss et al. | 260/112.5 |
| 4,382,922 | 5/1983 | Rivier et al. | 424/177 |
| 4,569,927 | 2/1986 | Rivier et al. | 514/15 |
| 5,169,932 | 12/1992 | Hoeger et al. | 530/313 |
| 5,296,468 | 3/1994 | Hoeger et al. | 530/313 |

OTHER PUBLICATIONS

Theobald et al, Journal of Chem. Soc., vol. 112, pp. 9624–9626, (1990).
Theobald et al, Journal of Med. Chem., vol. 34, pp. 2395–2402, (1991).
Rivier et al, BBRC, vol. 176(1), pp. 406–412, (1991).
Rivier et al, Journal of Medicinal Chemistry, vol. 35, pp. 4270–4278, (1992).
Webb et al, J. Heterocyclic Chem., vol. 19, pp. 1205–1206 (1982).
Croft, Handbook of Protein Sequence Analysis, 2nd ed., pp. 66–83, (Sep. 1979).

*Primary Examiner*—Christina Y. Chan
*Assistant Examiner*—T. D. Wessendorf
*Attorney, Agent, or Firm*—Fitch, Even, Tabin & Flannery

[57] ABSTRACT

Peptides which include unnatural amino acids and which either promote or inhibit the secretion of gonadotropins by the pituitary gland and inhibit the release of steroids by the gonads. Administration of an effective amount of such peptides that are GnRH antagonists prevents ovulation of female mammalian eggs and/or the release of steroids by the gonads and may be used to treat steroid-dependent tumors. The agonists can be used for control of reproduction processes, to treat precocious puberty, endometriosis, and the like. The peptides are analogs of the decapeptide GnRH wherein there is at least one residue of an unnatural amino acid in the 3-, 5-, 6- and/or 8-positions. Unnatural amino acids having the following formula are incorporated in a preferred group of synthesized peptides:

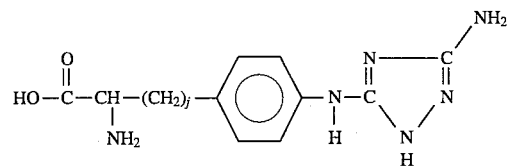

with $j = 1$, 2 or 3.

Methods for synthesizing such peptides having the triazole side chains are disclosed wherein one side chain modification (or two simultaneously) is carried out on an amino-substituted phenylalanine residue in a peptide chain which is a part of a peptidoresin.

18 Claims, No Drawings

GNRH ANALOGS

This invention was made with Government support under grant number HD-13527 and contracts NO1-HD-1-3100 and NO1-HD-0-2906 awarded by the National Institutes of Health. The Government has certain rights in this invention.

This application is a continuation-in-part of U.S. Ser. No. 08/078,965, filed Jun. 17, 1993, and a continuation-in-part of U.S. Ser. No. 08/006,729, filed Jan. 21, 1993, now U.S. Pat. No. 5,296,468 which is a continuation-in-part of U.S. Ser. No. 07/669,695, filed Mar. 14, 1991, now abandoned, which is a is a continuation-in-part of U.S. Ser. No. 07/545,239, filed Jun. 27, 1990, now U.S. Pat. No. 5,169,932, which is a continuation-in-part of U.S. Ser. No. 07/428,827, filed Oct. 30, 1989, now abandoned.

This invention relates generally to peptides having unnatural amino acids and to the preparation of new unnatural amino acids, which may be derived from diamino acids, such as Lys, Orn, Dpr and Dbu. More particularly, it relates to GnRH analogs having such unnatural amino acids which can be prepared either in such fully assembled peptides or for incorporation into such peptides as a part of the usual chain elongation synthesis process.

In one more particular aspect, the present invention relates to peptides which inhibit gonadal function and the release of the steroidal hormones, progesterone and testosterone and also to peptides which promote the release of such steroids, as well as to methods of promoting or preventing ovulation.

BACKGROUND OF THE INVENTION

The pituitary gland is attached by a stalk to the region in the base of the brain known as the hypothalamus. In particular, follicle stimulating hormone (FSH) and luteinizing hormone (LH), sometimes referred to as gonadotropins or gonadotropic hormones, are released by the pituitary gland. These hormones, in combination, regulate the functioning of the gonads to produce testosterone in the testes and progesterone and estrogen in the ovaries, and they also regulate the production and maturation of gametes.

The release of a hormone by the anterior lobe of the pituitary gland usually requires a prior release of another class of hormones produced by the hypothalamus. One of the hypothalamic hormones acts as a factor that triggers the release of the gonadotropic hormones, particularly LH, and this hormone is referred to herein as GnRH although it has also been referred to as LH—RH and as LRF. GnRH was isolated and characterized as a decapeptide some 20 years ago, and it was found that analogs of GnRH having a D-isomer instead of Gly in the 6-position, such as [D-Ala$^6$]-GnRH (U.S. Pat. No. 4,072,668) having the following formula:

pGlu-His-Trp-Ser-Tyr-D-Ala-Leu-Arg-Pro-Gly-NH$_2$, have greater binding strength to the receptor and greater biological potency than the native hormone.

Peptides are compounds which contain two or more amino acids in which the carboxyl group of one acid is linked to the amino group of the other acid. The formula for GnRH, as represented above, is in accordance with conventional representation of peptides where the amino terminus appears to the left and the carboxyl terminus to the right. The position of the amino acid residue is identified by numbering the amino acid residues from left to right. In the case of GnRH, the hydroxyl portion of the carboxyl group of glycine at the C-terminus has been replaced with an amino group(NH$_2$) i.e. the C-terminus is amidated. The abbreviations for the individual amino acid residues above are conventional and are based on the trivial name of the amino acid, e.g. pGlu is pyroglutamic acid, Glu is glutamic acid, His is histidine, Trp is tryptophan, Ser is serine, Tyr is tyrosine, Gly is glycine, Leu is leucine, Nle is norleucine, Orn is ornithine, Arg is arginine, Har is homoarginine, Pro is proline, Sar is sarcosine, Phe is phenylalanine, Ala is alanine, Val is valine, Nva is norvaline, Ile is isoleucine, Thr is threonine, Lys is lysine, Asp is aspartic acid, Asn is asparagine, Gln is glutamine, and Met is methionine. Except for glycine, amino acids of the peptides of the invention are of the L-configuration unless noted otherwise.

There are reasons for desiring to prevent ovulation in female mammalians, and the administration of GnRH analogs that are antagonistic to the normal function of GnRH have been used to suppress or delay ovulation. For this reason, analogs of GnRH which are antagonistic to GnRH are being investigated for their potential use as a contraceptive or for regulating conception periods. GnRH antagonists may also be used for the treatment of precocious puberty and endometriosis. The GnRH superagonists can also be used for these purposes. Such antagonists have also been found useful to regulate the secretion of gonadotropins in male mammals and can be employed to arrest spermatogenesis, e.g. as male contraceptives for treatment of male sex offenders, and for treatment of prostatic hypertrophy. More specifically, GnRH antagonists can be used to treat steroid-dependent tumors, such as prostatic and mammary tumors, and for the control of the timing of ovulation for in vitro fertilization. In the female, they can also be used to treat hirsutism.

On the other hand, GnRH agonists function in the same manner as GnRH in promoting the release of LH and FSH, and agonists which exhibit greater biopotency and/or longer duration of action are considered valuable.

In one aspect, it is desired to provide improved peptides which either are strongly antagonistic to endogenous GnRH and prevent secretion of LH and FSH and the release of steroids by the gonads of mammals or are strong agonists of GnRH. Of particular interest are compounds which are more effective in vivo when administered orally.

SUMMARY OF THE INVENTION

The present invention provides unnatural amino acids that can be prepared de novo or by modifying a previously prepared peptide, but which are preferably prepared as a part of a protected peptide-resin, containing a desired overall sequence which includes one or more amino acid residues having a side chain amino group which is to be modified. The resultant preferred amino acids have a side chain which contains either a modified guanidino group or a guanidino equivalent or a derivative that is obtained by further elucidation of a modified guanidino group, as set forth hereinafter, and most preferably it contains a triazole moiety.

In another particular aspect, the invention provides peptides which inhibit the release of gonadotropins in mammalians, including humans, and it also provides methods for inhibiting the release of steroids by the gonads of male and female mammalians. The invention also provides improved GnRH analogs which are strong agonists of GnRH and can be used to promote the reproduction processes of mammalians. As mentioned above, these GnRH antagonists may be used to inhibit the production of gonadotropins and sex hormones under various circumstances, including precocious puberty, hormone dependent neoplasia, dysmenorrhea, endometriosis and steroid-dependent tumors.

The invention provides unnatural amino acids having the following formula U*:

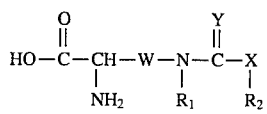

where W is $(CH_2)_n$ or

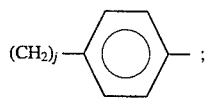

n is an integer from 1 to 6 and is preferably 1,2,3 or 4; j is 1,2 or 3; Y=N—CN, N—CONH$_9$, O, S or CH—NO$_2$, where R$_9$ is H, Ac, alkyl (preferably C$_1$ to C$_4$), naphthyl, pyridyl, pyrimidyl, pyrazinyl, indolyl, quinolinyl or imidazolyl, which alkyl and cyclic groups are unsubstituted or substituted (preferably by chloro, fluoro, bromo, amino, nitro, alkyl (C$_1$ to C$_4$) and alkoxy (C$_1$ to C$_4$)); X=NH, O, N$_3$, M$_1$—(CH$_q$)$_p$—M$_2$ or M$_1$—(CH$_2$)$_p$—M$_2$(CH$_2$)$_{p''}$—M$_3$, where M$_1$ is NR$_{10}$, N, O or CHR$_3$ wherein R$_3$ is methyl, ethyl, propyl, phenyl, pyridinyl, pyrimidinyl or purinyl; q=1 or 2; p, p' and p" are integers between 0 and 6; R$_{10}$ is H, methyl, ethyl, propyl, phenyl or substituted phenyl (preferably by Cl, F, NO$_2$ or NH$_2$); and M$_2$ and M$_3$=M$_1$, COOH, CONH$_2$, COOR$_3$ or CN (preferably X is NH or O); R$_1$=H, alkyl (preferably C$_1$ to C$_6$ and most preferably C$_1$ to C$_4$), modified alkyl (preferably C$_1$ to C$_5$, the terminal carbon of which is either substituted with NH$_2$, OH, Cl, Br or F or is replaced with CF$_3$ or CF$_2$CF$_3$), alkenyl (preferably C$_2$ to C$_4$), such as CH$_2$CH=CHR$_3$, alkynyl (preferably C$_2$ to C$_4$), such as CH$_2$C≡CR$_3$, aryl such as benzyl, tolyl, p-aminobenzyl (anilinyl) and pCl-benzyl or a direct bond to X; R$_2$=R$_1$, OH, NH$_2$, NHR$_1$, heterocycle (preferably as illustrated hereinafter) or desR$_2$, with R$_2$ being desR$_2$ when X=N$_3$. Optionally R$_2$ and X can be interconnected, or R$_1$ and R$_2$ can be connected to each other via a branched or unbranched methylene bridge of type —(CH$_2$)$_m$— or —(CH$_2$)$_m$—M—(CH$_2$)$_{m'}$—. In such an R$_1$-R$_2$ moiety, m and m' are integers from 1 to 6 and preferably from 1 to 3; and M=NH, O, S or CHR$_4$, wherein R$_4$ is lower alkyl or aryl and is preferably methyl, ethyl, propyl, phenyl or pCl-phenyl, with M preferably being O or S. Most preferably, when R$_1$ and R$_2$ are interconnected, they form a 5, 6, or 7-member heterocyclic ring with the "N—C—X" portion of the formula U*. If desired to form a cyclic peptide, XR$_2$ can contain a part of another diamino acid within the same peptide, e.g., the omega amino group of the 5-position residue can be so linked to such an unnatural amino acid residue in the 8-position.

Modification of the specified primary amino function of a given amino acid or peptide is carried out by treatment of either the appropriately protected peptide or the amino acid with an appropriate reagent(s). Peptides or amino acids where Y is N—CN (herein referred to as cyanoguanidines) are prepared by reaction of an amino group with diphenyl cyanocarbonimidate (I):

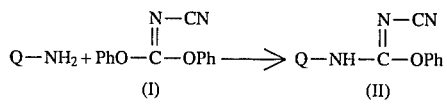

wherein "Q" is used to broadly represent either the major portion of a peptide or an amino acid having a primary amino group (such as the amino acid which is depicted above) as a part of formula U*.

The peptide or amino acid having the N-substituted-N'-cyano-O-phenylisourea moiety (II) can then be either isolated or further functionalized by reaction with a second nucleophile HXR$_2$ to produce cyanoguanidine-containing peptides or amino acids having the formula (III):

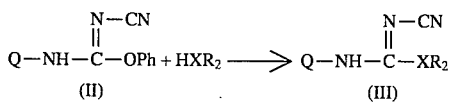

For example,

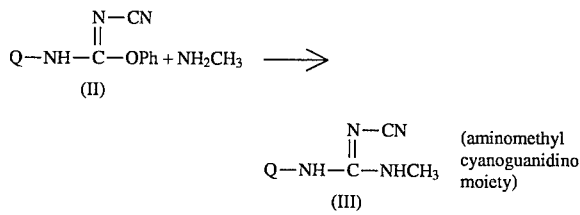

For example, where HXR$_2$=H$_2$N—CH$_2$-pyridine, the result is:

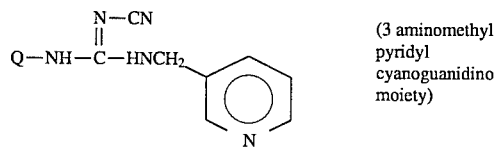

This group may also be referred to (IUPAC nomenclature) as N-g-cyano-N-g'-3-methylpyridylguanidino.

Such compounds can be hydrolyzed under acidic conditions to produce compounds which are also biopotent—for example:

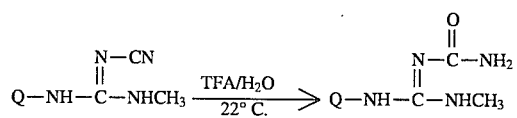

The hydrolyzed versions, referred to herein as including the N-g'-amido group, can also be synthesized directly by reacting phosgene derivates with moieties having a guanidino function.

If HXR$_2$ is an amino group of another peptide or protein, one will obtain a peptide-peptide dimer or peptide-protein dimer conjugated via the cyanoguanidine moiety. If HXR$_2$ is the N-terminal primary amino group or the side chain amino group of another amino acid in the same peptide, one will obtain a cyclic peptide (IV) linked via the cyanoguanidine moiety:

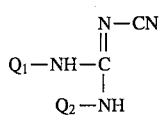

(IV)

wherein $Q_1$ and $Q_2$ represent the remainders of two amino acid residues in the same peptide. Cyclization via the cyanoguanidine derivative is preferably effected while a part of the peptidoresin, as opposed to subsequently cyclizing the linear peptide.

A special case arises when —$XR_2$ contains a second nucleophilic site and X has the general form:
$M_1$—$(CH_q)_p$—$M_2$ or $M_1$—$(CH_2)_{p'}$—$M_2$—$(CH_2)_{p''}$—$M_3$, where $M_1$, $M_2$ and $M_3$ are individually NH, N, O or $CHR_3$, with p, p', p" being 0,1,2 or 3 and q being 1 or 2. Examples of such nucleophiles include $H_2NNH_2$, $CH_3HNNH_2$, $CH_3HNNHCH_3$, $H_2NOH$, and $H_2N$—$CH_2$—$CH_2OH$. In this case, the cyanoguanidine moiety that is formed can be converted into the corresponding heterocycle (V) which forms from the initial intermediate by reaction of the omega amino group with the cyano group such as:

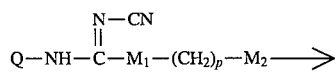

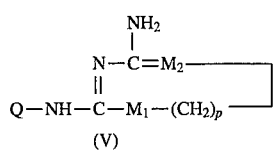

(V)

For example, where —$XR_2$=—$HNNH_2$,

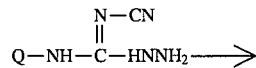

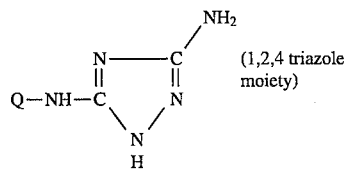

(1,2,4 triazole moiety)

Furthermore, where —$XR_2$=—$CH_3NNHCH_3$

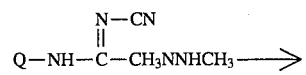

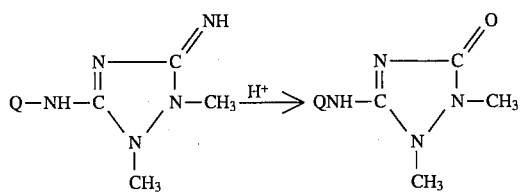

which may then undergo hydrolysis, as indicated above.

Where $XR_2$ contains a carboxylic acid group or the equivalent, particularly a carboxylic ester or carboxylic amide, a heterocyclic moiety, such as a saturated pyrimidine-like moiety (VI), is formed, by reaction of the carboxylic group with the secondary amino group ($R_1$), when $M_1$ is N, and similar 6-membered heterocyclic moieties are formed when $M_1$ is O or S. For example, $R_2$ may be $M_1$—$(CH_2)_p$—$M_2$ with $M_2$=COOH, COOCH$_3$ or CONH$_2$ and p being an integer between 1 and 4. For instance in such a case where an aliphatic carboxylic acid group is present and p=2:

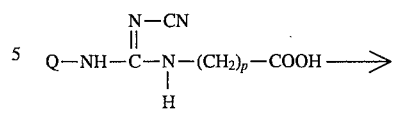

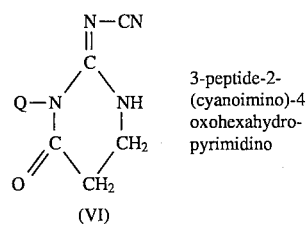

3-peptide-2-(cyanoimino)-4-oxohexahydro-pyrimidino (VI)

If $R_2$ includes an ortho-substituted aromatic carboxylic acid, e.g. benzoic acid (q=1 and p=6), the corresponding quinazoline-like species (VII) is formed:

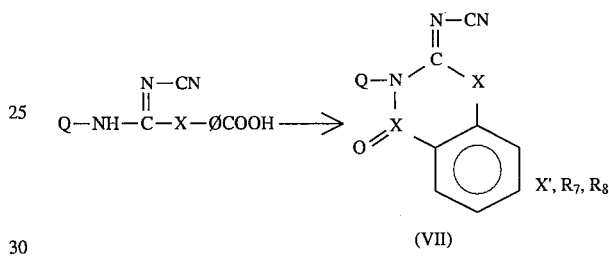

(VII)

Such benzoic acid may be further substituted, and such substitutions may in any of the other 4 ring positions, as shown, creating the corresponding substituted quinazoline-like moiety which is considered to be equivalent to the unsubstituted. X' may be H, Cl, Br, F, NHCH$_3$ or SCH$_3$, and $R_7$ and $R_8$ may be H, CH$_3$ or CH$_2$CH$_3$.

The molecules wherein X=$N_3$ and $R_2$ is des$R_2$ (i.e. deleted) are useful for photolabeling because of the activity of the —$N_3$ group and are formed by reacting the moiety (II) with sodium azide (NAN$_3$).

Peptides wherein Y is O (herein referred to as ureas) or S (referred to as thioureas) are prepared by the well known procedure in which the desired side chain amino group is treated with an appropriate isocyanate or thioisocyanate to obtain such ureas or thioureas.

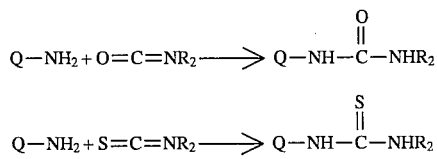

Peptides or amino acids wherein Y is CH—NO$_2$ (herein referred to as diaminonitroethylenes) are prepared by conversion of the corresponding urea to a carbodiimide:

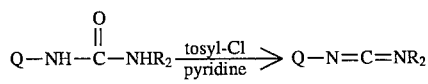

followed by treatment with nitromethane anion (prepared by the action of sodium hydride on nitromethane in dry DMF) as disclosed generally in F. Meimas, et al., *Synthesis*, 509–510 (1985):

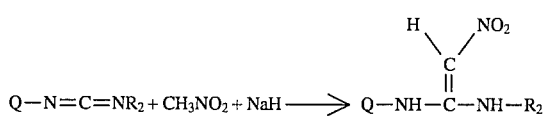

An alternative synthesis that may be used is as follows:

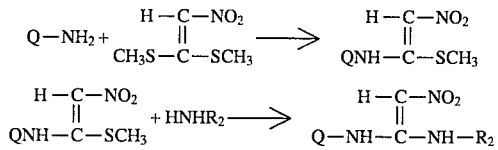

Generally, in accordance with the present invention, peptides are synthesized which are antagonists or agonists of GnRH. Antagonists strongly inhibit the secretion of gonadotropins by the pituitary gland of mammals, including humans, and/or inhibit the release of steroids by the gonads. Agonists strongly promote such secretion or release. These peptides are analogs of GnRH containing one or more unnatural amino acids of the formula U* in the 3-position, the 5-position, the 6-position and/or the 8-position. When U* is in the 3-and/or 6-position, it is always in the form of a D-isomer; whereas when U* is in the 5- and/or 8-position, it is always in the form of an L-isomer. An antagonist should have a 1-position substitution, such as dehydroPro or β-(1-or 2-naphthyl)-D-alanine (hereinafter β-D-1NAL or β-D-2NAL), a 2-position substitution in the form of a modified D-Phe and a 3-position substitution, preferably in the form of substituted or unsubstituted D-Trp, D-3PAL, β-D-NAL or the residue of a D-isomer amino acid U*. The 5-position may be occupied by (a) Tyr, (b) a halogenated or methylated Phe or Tyr, (c) Arg, (d) Lys in which the side chain amino group is acylated by 3-carboxypyridine (nicotinic acid) or by 2 or 4-carboxypyridine, i.e. Lys(cpd), preferably Lys(3cpd) which is also referred to as Lys(Nic), (e) His or (f) the residue of an L-isomer amino acid U*. Agonists have a 6-position substitution which is the residue of the D-isomer U*, and the antagonists may have a D-isomer U* or such a substituted or acylated D-Lys in the 6-position. Instead of Leu in the 7-position, both may have Nle, NML, Phe, Nva, Met, Tyr, Trp or PAL, of which the Phe or Trp may be substituted. The antagonists may also have an optional substitution in the 8-position, which preferably may be the L-isomer U* or isopropyl Lys, i.e., ILys or Lys(Ipr) wherein the side chain amino group is substituted by isopropyl, and a substitution in the 10-position such as D-Ala. At least one residue of a D-isomer amino acid of the formula U* is most preferably present in each peptide of the invention.

Modified D-Phe in the 2-position provides increased antagonistic activity as a result of the specific modifications present in the benzene ring. Single substitutions for hydrogen in the ring are preferably made in the para- or 4-position, but might be in either the 2- or 3-position also; the substitutions are selected from chloro, fluoro, bromo, methyl, methoxy and nitro, with chloro, fluoro and nitro being preferred. Dichloro substitutions are in the 2,4 or 3,4 positions in the ring. The α-carbon atom may also be methylated, e.g. ($C^\alpha$Me/4Cl)Phe. The 1-position substituent is preferably modified so that its α-amino group contains an acyl group, such as formyl(For), acetyl(Ac), acrylyl(Acr), vinylacetyl-(Vac) or benzoyl(Bz), with acetyl and acrylyl being preferred and with acetyl being most preferred. PAL and D-PAL represent the L- and D-isomers of pyridylalanine where the β-carbon of Ala is linked to the 2-, 3- or 4-position, preferably to the 3-position, on the pyridine ring. When β-D-NAL is present in the 1-position and $R_5$ is not Arg, a hydrophilic D-amino acid residue, such as $4NH_2$-D-Phe, 4-guanidino-D-Phe, D-His, D-Lys, D-Orn, D-Arg, D-Har-(Homoarginine) or D-PAL is preferably present in the 6-position if U* is not present. When dehydroPro is present in the 1-position, D-PAL or a D-isomer of a lipophilic amino acid, such as D-Trp, D-Phe, For-D-Trp, $NO_2$-D-Trp, D-Leu, D-Ile, D-Nle, D-Tyr, D-Val, D-Ala, dialkyl Arg, dialkyl Har, D-Ser(OtBu), β-D-NAL or (imBzl)D-His is preferably in the 6-position, if U* is not present.

These GnRH analogs are very soluble at a pH just below physiological pH, i.e. about 4.5 to about 6, and thus can be formulated and administered in concentrated form, greatly facilitating administration at a pH of about 5 to 7.4 which is presently preferred. The agonists are substantially more potent than native GnRH in effecting release of LH and FSH. The antagonists inhibit ovulation of female mammals when administered at low levels at proestrus and are also effective to cause resorption of fertilized eggs if administered shortly after conception. The antagonists are also effective for the contraceptive treatment of male mammals and the treatment of steroid-dependent tumors. Certain of the antagonists are surprisingly long-acting in their suppression of LH levels following administration, and certain have a particularly low side effect in respect of histamine release.

DETAILED DESCRIPTION OF THE PREFERRED EMBODIMENTS

As previously mentioned, the unnatural amino acids (which can be L- or D-isomers) are represented by the formula U*:

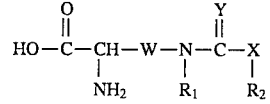

wherein W, X, Y, $R_1$ and $R_2$ are as defined previously, and there is at least one such residue (preferably a D-isomer) in each peptide of the invention.

More specifically, the GnRH antagonists of the present invention are represented by the following Formula ($F_1$):

G-$AA_1$-(A)D-Phe-$AA_3$-Ser-$AA_5$-$AA_6$-$AA_7$-$AA_8$-Pro-$AA_{10}$ wherein G is hydrogen or an acyl group having 7 or less carbon atoms; $AA_1$ is dehydroPro, D-pGlu, (A) D-Phe, (B) D-Trp, Pro, or β-D-NAL; A is H, Cl, F, $NO_2$, $CH_3$, $OCH_3$, $C^\alpha$Me/4Cl, $Cl_2$ or Br; B is H, $NO_2$, $NH_2$, $OCH_3$, F, Cl, Br, $CH_3$, $N^{im}$For or $N^{im}$Ac; $AA_3$ is U*, D-PAL, β-D-NAL or (B) D-Trp; $AA_5$ is U*, Tyr, (C)Arg, Lys(cpd), Orn(cpd), Dbu(cpd), Dpr(cpd), (A) Phe, (3I)Tyr or His; $AA_6$ is U*, β-D-NAL, (B)D-Trp, (A')D-Phe, (D)D-Orn, (D)D-Lys, (D) D-Dbu, (D) D-Dpr, D-Har, D-Tyr, (E) D-His, D-PAL, (C) D-Arg or a suitable lipophilic D-isomer; A' is A, $NH_2$, $NHCH_3$ or gua; C is H or lower alkyl; D is G, cpd or an aryl group; E is H, imBzl or dinitrophenol; $AA_7$ is Nle, Leu, NML, (A)Phe, Met, Nva, Tyr, (B)Trp or PAL; $AA_8$ is U*, (C')Arg, (C')Har or ILys; C' is H or di-lower alkyl; $AA_{10}$ is D-Ala-$NH_2$, Gly-$NH_2$, AzaGly-$NH_2$ or NH(R); R is lower alkyl, preferably $CH_2CH_3$; and U* is as defined above. When $AA_1$ is β-D-NAL and $AA_5$ is not Arg, then $AA_6$ is preferably U*, $4-NH_2$-D-Phe, D-Lys, D-Orn, D-Har, D-His, 4-gua-D-Phe, D-PAL or D-Arg.

By dehydroPro is meant 3,4 dehydroproline, $C_5H_7O_2N$. By β-D-NAL is meant the D-isomer of alanine which is substituted by naphthyl on the β-carbon atom, i.e., also 3-D-NAL. Preferably β-D-2NAL is employed wherein the attachment to naphthalene is at the 2-position on the ring structure; however, β-D-1NAL may also be used. The preferred 1-position residues are β-D-NAL, substituted D-Phe and optionally substituted D-Trp. PAL represents alanine which is substituted by pyridyl on the β-carbon atom; preferably the linkage is to the 3-position on the pyridine ring. When substituted D-Trp is employed, single substitutions for hydrogen are preferably made in either the 5- or 6-position, which are selected from chloro, fluoro, bromo, methyl, amino, methoxy and nitro, with chloro, fluoro and nitro being preferred. Alternatively, the indole nitrogen may be acylated, e.g. with formyl ($N^{in}$For- or 1For-) or with acetyl. D-3PAL, $N^{in}$For-D-Trp and $6NO_2$-D-Trp are the preferred residues for the 3-position although D-Trp is also often used. When U* is not in the 5-position, Tyr, Arg or Lys(cpd) preferably is present. By NML is meant $N^\alpha CH_3$-L-Leu. By Dbu is meant alpha, gamma diamino butyric acid, and by Dpr is meant α,β diamino propionic acid. By Aph is meant $4NH_2$Phe; aminohomophenylalanine and aminohomohomophenylalanine are considered to be equivalents thereof. Instead of being in the para- or 4-position, the amino substitution may also be in the meta or ortho position. When dehydroPro is present in the 1-position, Tyr or U* is preferably present in the 5-position and a lipophilic residue is in the 6-position. By 4-gua-D-Phe is meant a residue of D-Phe having guanidine substituted in the para-position. By Aza-Gly-$NH_2$ is meant $NHNHCONH_2$. The guanidino group of an Arg residue in the 5- or 6-position may be substituted by lower alkyl, i.e. 1 to 4 carbon atoms, e.g., propyl(Pr). When D-Lys, D-Dbu, D-Dpr or D-Orn is present in the 6-position and it is not a part of an unusual amino acid U*, its side-chain-amino group may be acylated by an acyl group which may be aliphatic, heterocyclic or aromatic, e.g. nicotinic acid, or may be substituted by an aryl group having not more than 1 phenyl ring. When U* is not present in the 6-position, it is preferably D-PAL or D-Lys(cpd). The 7-position residue is preferably Leu, NML, Nle or Phe. If the 8-position residue is not U*, it is preferably ILys.

More specifically the GnRH agonists of the invention are represented by the following Formula ($F_2$): pGlu-His-Trp-Ser-Tyr-U*-$AA_7$-Arg-Pro-$AA_{10}$, wherein U*, $AA_7$ and $AA_{10}$ are as defined hereinbefore. Preferably $AA_7$ is Leu or NML, $AA_{10}$ is $NHCH_2CH_3$ and U* includes a residue of amino-substituted Phe (or its equivalent, e.g homophenylalanine).

Overall, the invention thus provides GnRH analogs having the Formula ($F_3$):

G-AA-$AA_2$-AA'-Ser-$AA_5$-$AA_6$-$AA_7$-$AA_8$-Pro-$AA_{10}$ wherein AA is pGlu or $AA_1$; $AA_2$ is His or (A)D-Phe; AA' is Trp or $AA_3$; and all others are as defined hereinbefore.

One preferred subgenus of GnRH antagonists has the following formula:

Ac-$AA_1$-(A)D-Phe-$AA_3$-Ser-$AA_5$-$AA_6$-$AA_7$-$AA_8$-Pro-$AA_{10}$ wherein $AA_1$ is (A)D-Phe, (B)D-Trp or β-D-NAL; A is H, 4Cl, 4F, $4NO_2$, $4CH_3$, $4OCH_3$, $C^\alpha Me/4Cl$, $2,4Cl_2$ or 4Br; B is H, $6NO_2$, $6NH_2$, $6OCH_3$, 6F, 6Cl 6Br, $6CH_3$, $N^{in}$For or $N^{in}$Ac; $AA_3$ is U*, D-PAL, β-D-NAL or (B)D-Trp; $AA_5$ is U*, Lys(cpd) or Tyr; $AA_6$ is U*, β-D-NAL, $4NH_2$D-Phe, (B)D-Trp, D-Lys(cpd), D-PAL or D-Arg; $AA_7$ is Nle, Leu, NML or Phe; $AA_8$ is U*, ILys, or Arg; $AA_{10}$ is D-Ala-$NH_2$, Gly-$NH_2$, $NHNHCONH_2$ or NH(R); R is lower alkyl; and U* is either

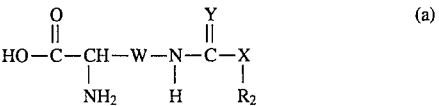

where W is $(CH_2)_n$ or

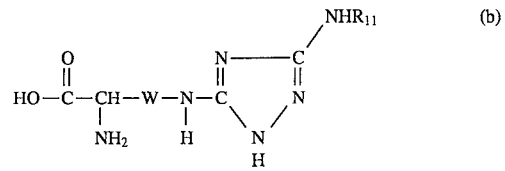

n is an integer from 1 to 4; j is 1,2 or 3; X is NH or O; Y is N—CN or N—$CONH_9$ where $R_9$ is H or lower alkyl; $R_2$ is lower alkyl, cyclohexyl, phenyl, pyridyl, methyl pyridyl or histaminyl; or

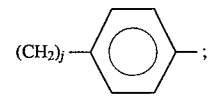

where W is defined as above and $R_{11}$ is H or an acyl radical having 1 to 6 carbon atoms; provided, however, that at least one of $AA_3$, $AA_5$, $AA_6$ and $AA_8$ is U*.

Another preferred subgenus of GnRH antagonists has the following formula:
Ac-$AA_1$-(A)D-Phe-U*-Ser-$AA_5$-AA6-AA7-$AA_8$-Pro-$AA_{10}$ wherein $AA_1$ is (A) D-Phe, (B) D-Trp or β-D-NAL; A is H, 4Cl, 4F, $4NO_2$, $4CH_3$, $4OCH_3$, $C^\alpha Me/4Cl$, $2,4Cl_2$ or 4Br; B is H, $6NO_2$, $6NH_2$, $6OCH_3$, 6F, 6Cl, 6Br, $6CH_3$, $N^{in}$For or $N^{in}$Ac; $AA_5$ is Lys(cpd) or Tyr; $AA_6$ is β-D-NAL, $4NH_2$D-Phe, (B) D-Trp, D-Lys (cpd), D-PAL or D-Arg; $AA_7$ is Nle, Leu, NML or Phe; $AA_8$ is ILys or Arg; $AA_{10}$ is D-Ala-$NH_2$, Gly-$NH_2$, $NHNHCONH_2$ or NH(R); R is lower alkyl; and U* is either

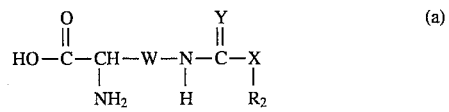

where W is $(CH_2)_n$ or

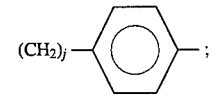

n is an integer from 1 to 4; j is 1,2 or 3 (preferably 1); X is NH or O; Y is N—CN or N—$CONH_9$ where $R_9$ is H or lower alkyl ($C_1$–$C_3$), preferably H; $R_2$ is lower alkyl ($C_1$–$C_6$), cyclohexyl, phenyl, pyridyl, methyl pyridyl or histaminyl; or

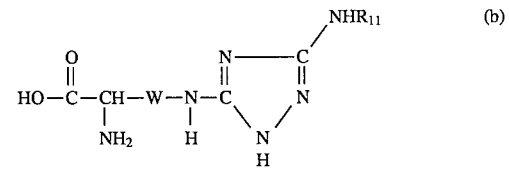

where W is defined as above and $R_{11}$ is H or an acyl radical having 1 to 3 carbon atoms, preferably acetyl.

Still another preferred subgenus of GnRH antagonists has the formula:
Ac-β-D-2NAL-(4Cl)D-Phe-U*-Ser-Tyr-D-3PAL-Leu-Lys(isopropyl)-Pro-D-Ala-$NH_2$, wherein U* is a D-isomer having the formula either

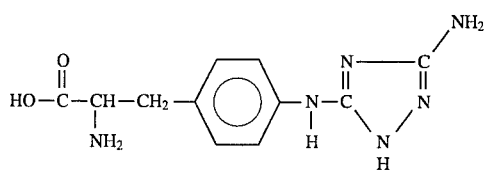

(a)

or

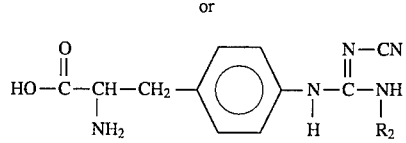

(b)

where $R_2$ is lower alkyl.

Yet another preferred subgenus of GnRH antagonists has the formula:
Ac-β-D-2NAL-(4Cl)D-Phe-D-3PAL-Ser-U*-U*-AA$_7$-Lys (isopropyl)-Pro-AA$_{10}$ wherein AA$_7$ is Leu or N$^α$CH$_3$Leu; AA$_{10}$ is D-Ala-NH$_2$, Gly-NH$_2$, or NHCH$_2$CH$_3$; and U* is either

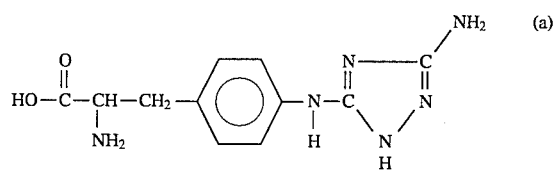

(a)

or

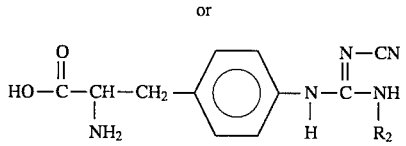

(b)

where $R_2$ is lower alkyl, pyridyl or methyl pyridyl; provided, however, that U* in the 6-position is always a D-isomer.

An additional preferred subgenus of GnRH antagonists has the formula:
Ac-β-D-2NAL-(4Cl)D-Phe-D-3PAL-Ser-U*-U*-AA$_7$-Lys (isopropyl)-Pro-AA$_{10}$ wherein AA$_7$ is Leu or N$^α$CH$_3$-Leu; AA$_{10}$ is D-Ala-NH$_2$, Gly-NH$_2$ or NHCH$_2$CH$_3$; and U* is

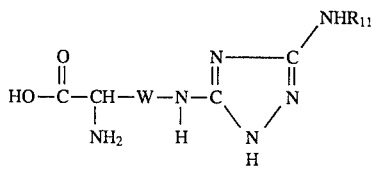

where W is $(CH_2)_n$ or

n is an integer from 1 to 6; and $R_{11}$ is H or an acyl radical having 1 to 6 carbon atoms; provided, however, U* in the 6-position is a D-isomer.

One more preferred subgenus of GnRH antagonists has the formula:
Ac-β-D-2NAL-(4Cl)D-Phe-D-3PAL-Ser-AA$_5$-AA$_6$-Leu-Lys (isopropyl)-Pro-D-Ala-NH$_2$ wherein AA$_5$ is U* or Lys(carboxypyridine); AA$_6$ is U* or D-Lys(carboxypyridine); and U* is

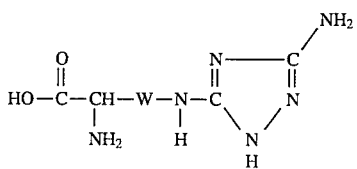

where W is $(CH_2)_n$ and n is 4; provided, however, that either AA$_5$ is U* or AA$_6$ is U*, with AA$_6$ always being a D-isomer.

The peptides of the present invention can be synthesized by classical solution synthesis, but are preferably synthesized by a solid phase technique. A chloromethylated resin or a hydroxymethylated resin may be used; however, a methylbenzhydrylamine(MBHA) resin, a benzhydrylamine (BHA) resin or some other suitable resin known in the art which directly provides a C-terminal amide or substituted amide upon cleavage is preferably employed when such a C-terminus is desired. For example, peptides having a substituted amide at the C-terminus are preferably synthesized using an N-alkylamino methyl resin as taught in U.S. Pat. No. 4,569,967, issued Feb. 11, 1986. Solid phase synthesis is conducted in a manner to stepwise add amino acids in the chain in the manner set forth in detail in the U.S. Pat. No. 4,211,693. Side-chain protecting groups, as are well known in the art, are preferably included as a part of any amino acid which has a particularly reactive side chain and optionally in the case of others, such as Trp, which amino acids are to be coupled in the chain being built upon the resin. Such synthesis provides the fully protected intermediate peptidoresin.

Chemical intermediates made generally in accordance with the invention may be represented by the formula: $X^1$-AA-AA$_2$($X^5$)-U$_3$-Ser($X^3$)-U$_5$-U$_6$-AA$_7$($X^2$ or $X^7$)-U$_8$-Pro-$X^8$ wherein: U$_3$ is either U' or AA' ($X^2$); U$_5$ is either U' or AA$_5$($X^4$ or $X^5$); U$_6$ is either U' or AA$_6$($X^4$ or $X^5$ or $X^6$); U$_8$ is either U' or AA$_8$($X^5$ or $X^6$); U' is either Lys ($X^a$), Aph ($X^a$), Orn ($X^a$), Dbu ($X^a$) or Dpr ($X^a$); $X^1$ is an α-amino protecting group of the type known to be useful in the art in the stepwise synthesis of polypeptides and when G in the desired peptide composition is a particular acyl group, that group may be used as the protecting group. Among the classes of α-amino protecting groups covered by $X^1$ are (1) acyl-type protecting groups, such as formyl(For), trifluoroacetyl, phthalyl, p-toluenesulfonyl(Tos), benzoyl(Bz), benzenesulfonyl, dithiasuccinoyl(Dts) o-nitrophenylsulfenyl-(Nps), tritylsulfenyl, o-nitrophenoxyacetyl, acrylyl(Acr), chloroacetyl, acetyl(Ac) and γ-chlorobutyryl; (2) aromatic urethan-type protecting groups, e.g., benzyloxycarbonyl(Z), fluorenylmethyloxycarbonyl(Fmoc) and substituted benzyloxycarbonyl, such as p-chlorobenzyloxy-carbonyl(ClZ), p-nitrobenzyloxycarbonyl, p-bromobenzyloxycarbonyl and p-methoxybenzyloxycarbonyl; (3) aliphatic urethan protecting groups, such as tertbutyloxycarbonyl(Boc), diisopropylmethoxycarbonyl, isopropyloxycarbonyl, ethoxycarbonyl and allyloxycarbonyl; (4) cycloalkyl urethan-type protecting groups, such as cyclopentyloxycarbonyl, adamantyloxycarbonyl and cyclohexyloxycarbonyl; (5) thiourethan-type protecting groups, such as phenylthiocarbonyl; (6) alkyl-type protecting groups, such as allyl(Aly), triphenylmethyl(trityl) and benzyl(Bzl); (7) trialkylsilane groups, such as trimethylsilane. The preferred α-amino protecting group is Boc when X is hydrogen.

$X^2$ is hydrogen or a protecting group for the indole nitrogen of Trp, such as Bz, Ac or For. In many syntheses there is no need to protect Trp, and such protection is not used if acylated D-Trp is present elsewhere in the peptide.

$X^3$ is hydrogen or a protecting group for the hydroxyl side chain of Ser or Thr, e.g. Ac, Bz, trityl, DCB or benzyl ether(Bzl) and is preferably Bzl.

$X^4$ is hydrogen or a protecting group for the phenolic hydroxyl group of Tyr selected from the group consisting of tetrahydropyranyl, tert-butyl, trityl, benzyl, Z, 2-bromobenzyloxycarbonyl(2BrZ) and 2,6-dichlorobenzyl(DCB). 2BrZ is preferred.

$X^5$ is a protecting group for a side chain guanidino group, such as that in Arg or Har, or for the imidazole group of His, such as nitro, Tos, trityl, adamantyloxycarbonyl, Z and 2,4-dinitrophenol(Dnp), or $X^5$ may be hydrogen, which means there is no protection on the side chain group atoms. Tos is generally preferred.

$X^6$ is a protecting group for an amino side chain group, primary or secondary amino, such as Z or 2ClZ; $X^a$ is a subclass of $X^6$ comprising such protecting groups that can be removed without removing other side chain protecting groups so as to allow the omega-amino group to thereafter take part in the reactions to build the unnatural amino-acid residue. Preferably a base-labile group, such as Fmoc, methylsulfonylethyloxycarbonyl(Msc) or trifluoroacetyl(Tfa), is used; however, it may also be possible to use a hydrazine-labile group such as phthaloyl,

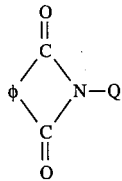

or a thiolabile group such as Nps or Dts.

$X^7$ is hydrogen or a protecting group for Met, such as oxygen; Met is generally left unprotected.

$X^8$ may be Gly-NH-[resin support], D-Ala-NH- [resin support] or N(A)-[resin support]; $X^8$ may also be an amide either of Gly or of D-Ala or a substituted amide attached directly to Pro or NHNHCONH$_2$.

The criterion for selecting side chain protecting groups for $X^2$–$X^7$ is that the protecting group should be stable to the reagent under the reaction conditions selected for removing the α-amino protecting group (preferably Boc) at each step of the synthesis. Protecting groups generally should not be split off under coupling conditions but should be removable upon completion of the synthesis of the desired amino acid sequence under reaction conditions that will not alter the peptide chain.

When the $X^8$ group is Gly-NH-[resin support] or D-Ala-NH-[resin support], an amide bond connects Gly or D-Ala to a BHA resin or to a MBHA resin. When the $X^8$ group is N(A)-[resin support], a substituted amide bond connects Pro to an N-alkylaminomethyl (NAAM) resin. When $X^8$ is AzaGly-NH$_2$, the peptide is preferably made by classical solution synthesis, as disclosed in U.S. Pat. No. 4,234,571.

When G is acetyl, for example, in the final formula, a reaction is preferably carried out with the peptide on the resin (after deblocking the α-amino group while the side-chain groups remain protected), e.g. by reacting with acetic acid in the presence of diisopropyl or dicyclohexyl carbodiimide (DIC or DCC) or preferably with acetic anhydride or by another suitable reaction as known in the art.

In one aspect, the invention particularly provides a method for making a GnRH antagonist peptide having the formula:

G-AA-AA$_2$-AA$_3$-Ser-AA$_5$-AA$_6$-AA$_7$-AA$_8$-Pro-AA$_{10}$,
wherein at least one of AA$_5$ and AA$_6$ is U* and the symbols are as set forth hereinbefore, which method comprises (a) forming an intermediate peptide having the formula:

$X^1$-AA-AA$_2$($X^5$)-AA$_3$($X^2$)-Ser($X^3$)-Aph($X^8$)-D-Aph($X^8$)-AA$_7$($X^2$ or $X^7$)-AA$_8$($X^5$ or $X^6$)-Pro-$X^8$ wherein: $X^1$ is hydrogen or an α-amino protecting group; $X^2$ is hydrogen or a protecting group for an indole nitrogen; $X^3$ is a protecting group for a hydroxyl group of Ser or Thr; $X^4$ is hydrogen or a protecting group for a phenolic hydroxyl group of Tyr; $X^5$ is either hydrogen or a protecting group for a guanidino or imidazole side chain; $X^6$ is a protecting group for a primary amino side chain of which $X^a$ is a subgroup that is removable without removing other protecting groups; $X^7$ is hydrogen or a protecting group for Met; $X^8$ is Gly-NH-[resin support] or D-Ala-NH-[resin support]; (b) removing $X^a$ to deprotect side chain primary amino groups of the Aph residues of said intermediate peptide; (c) reacting said deprotected side chain primary amino group to build said residue into one having a triazole moiety; and (d) splitting off any remaining groups $X^1$ to $X^7$ and/or cleaving from resin support included in $X^8$.

Purification of the peptide is effected by ion exchange chromatography on a CMC column, followed by partition chromatography using the elution system: n-butanol;0.1N acetic acid (1:1 volume ratio) on a column packed with Sephadex G-25, or by using HPLC, as known in the art and specifically set forth in J. Rivier, et al. *J. Chromatography,* 288 (1984) 303–328.

The antagonists of the invention are effective at levels of less than 100 micrograms per kilogram of body weight, when administered subcutaneously at about noon on the day of proestrus, to prevent ovulation in female rats. For prolonged suppression of ovulation, it may be necessary to use dosage levels in the range of from about 0.1 to about 2.5 milligrams per kilogram of body weight. These analogs are particularly soluble at physiological pHs and thus can be prepared as relatively concentrated solutions for administration. The antagonists are also effective to arrest spermatogenesis when administered to male mammals on a regular basis and can thus be used as contraceptives. Since these compounds will reduce testosterone levels (an undesired consequence in the normal, sexually active male), it may be reasonable to administer replacement dosages of testosterone along with the GnRH antagonist. These antagonists can also be used to regulate the production of gonadotropins and sex steroids for other purposes as indicated hereinbefore.

In the following formulas, the U* residues are defined in terms of the original amino acid residue having a side chain amino group plus the modification in question which is set forth in the accompanying parentheses. Preferably, the original residue is incorporated in the main peptide chain, for example Lys or D-Lys or Orn, Dbu, Dpr or a D-isomer thereof, and is modified while a part of the peptide chain that is still attached to the resin to form the desired residue of the amino acid U*. However, as indicated hereinbefore, the suitably protected unnatural amino acid U* can be added as a part of the usual chain elongation process.

With respect to modified side chain amino groups of the amino acids Lys, Orn, Dbu and Dpr, the following abbreviations are used:

act=acetyl aminotriazole
bcg=aminobutyl cyanoguanidino
bzcg=aminobenzyl cyanoguanidino
bur=N-g-amido, N-g'-butylguanidino
chcg=aminocyclohexyl cyanoguanidino
ecg=aminoethyl cyanoguanidino
icg=aminoisopropyl cyanoguanidino hcg=aminohexyl cyanoguanidino hicg=histaminyl cyanoguanidino (ethylimidazole)

mcg=aminomethyl cyanoguanidino ncg=aminoethyl(1 or 2)naphthyl cyanoguanidino mncg=aminomethyl(1 or 2)naphthyl cyanoguanidino Ocg=O-phenyl cyanoguanidino pcg=aminopropyl cyanoguanidino Sbcg=thiobutyl cyanoguanidino tcg=3-amino 1,2,4 triazole trcg=indole ethylamino cyanoguanidino(tryptamino cyanoguanidino)

mpcg=aminomethyl pyridyl cyanoguanidino (number indicates position of aminomethyl group on pyridyl ring)

The following Examples illustrate a large number of peptides embodying various features of the invention. All of these peptides include at least one D-isomer amino acid residue.

EXAMPLE I

Peptides as indicated in TABLE I having the formula: Ac-β-D-2NAL-(4Cl)D-phe-D-3PAL-Ser-$AA_5$-$AA_6$-Leu-$AA_8$-Pro-D-Ala-$NH_2$ are prepared by the solid-phase procedure referred to above.

TABLE I

|    | $AA_5$    | $AA_6$      | $AA_8$   |
|----|-----------|-------------|----------|
| 1  | Lys(icg)  | D-Lys(icg)  | ILys     |
| 2  | Lys(mcg)  | D-Lys(mcg)  | "        |
| 3  | Lys(chcg) | D-Lys(chcg) | "        |
| 4  | Lys(tcg)  | D-Lys(tcg)  | "        |
| 5  | Lys(pcg)  | D-Lys(pcg)  | "        |
| 6  | Lys(2mpcg)| D-Lys(2mpcg)| "        |
| 7  | Lys(3mpcg)| D-Lys(3mpcg)| "        |
| 8  | Lys(4mpcg)| D-Lys(4mpcg)| "        |
| 9  | Lys(hcg)  | D-Lys(hcg)  | "        |
| 10 | Lys(ecg)  | D-Lys(ecg)  | "        |
| 11 | Lys(Ocg)  | β-D-2NAL    | "        |
| 12 | Lys(bcg)  | "           | "        |
| 13 | Lys(Nic)  | D-Lys(Nic)  | Lys(bcg) |
| 14 | Lys(bcg)  | β-D-2NAL    | "        |
| 15 | Lys(bcg)  | D-Lys(bcg)  | Arg      |
| 16 | Tyr       | β-D-2NAL    | Lys(icg) |

For purposes of an example, a representative solid phase synthesis of peptide No. 1 above, which is referred to as [Ac-β-D-$2NAL^1$, (4Cl)D-$Phe^2$, D-$3PAL^3$, Lys$(icg)^5$, D-Lys$(icg)^6$, $ILys^8$, D-$Ala^{10}$]-GnRH is set forth hereinafter. This peptide has the following formula:
Ac-β-D-2NAL-(4Cl)D-Phe-D-3PAL-Ser-Lys(isopropyl cyanoguanidino)-D-Lys(isopropyl cyanoguanidino)-Leu-Lys (isopropyl)-Pro-D-Ala-$NH_2$.

An MBHA resin is used, and Boc-protected D-Ala is coupled to the resin over a 2-hour period in $CH_2Cl_2$ using a 3-fold excess of Boc derivative and DCC as an activating reagent. The D-Ala residue attaches to the MBHA residue by an amide bond.

Following the coupling of each amino acid residue, washing, deblocking and coupling of the next amino acid residue is carried out in accordance with the following schedule using an automated machine and beginning with about 5 grams of resin:

| STEP | REAGENTS AND OPERATIONS | MIX TIMES MIN. |
|------|--------------------------|----------------|
| 1  | $CH_2Cl_2$ wash-80 ml. (2 times) | 3 |
| 2  | Methanol(MeOH) wash-30 ml. (2 times) | 3 |
| 3  | $CH_2Cl_2$ wash-80 ml. (3 times) | 3 |
| 4  | 50 percent TFA plus 5 percent 1,2-ethanedithiol in $CH_2Cl_2$-70 ml. (2 times) | 10 |
| 5  | Isopropyl alcohol + 1% ethanedithiol wash-80 ml. (2 times) | 3 |
| 6  | TEA 12.5 percent in $CH_2Cl_2$-70 ml. (2 times) | 5 |
| 7  | MeOH wash-40 ml. (2 times) | 2 |
| 8  | $CH_2Cl_2$ wash-80 ml. (3 times) | 3 |
| 9  | Boc-amino acid (10 mmoles) in 30 ml. of either dimethylformamide(DMF) or $CH_2Cl_2$, depending upon the solubility of the particular protected amino acid, (1 time) plus DIC or DCC (10 mmoles) in $CH_2Cl_2$ | 30–300 |
| 10 | MeOH wash-40 ml. (2 times) | 3 |
| 11 | Triethylamine(TEA) 12.5 percent in $CH_2Cl_2$-70 ml. (1 time) | 3 |

After step 3, an aliquot may be taken for a ninhydrin test as well known in the art: if the test is negative, proceed to step 4 for removal of BOC-group prior to coupling of the next amino acid; if the test is positive or slightly positive, repeat steps 9 through 11.

The above schedule is used for coupling of each of the amino acids of the peptide of the invention after the first amino acid has been attached. $N^\alpha$Boc protection is used for each of the remaining amino acids throughout the synthesis. $N^\alpha$Boc-β-D-2NAL is prepared by a method known in the art, e.g. as described in detail in U.S. Pat. No. 4,234,571, issued Nov. 18, 1980 or commercially available from SyntheTech, Oregon, U.S.A. The side chains of Lys in the 5-position and of D-Lys in the 6-position are protected with Fmoc. Bzl (benzyl ether) is used as a side chain protecting group for the hydroxyl group of Ser. Boc-Lys(Ipr) is used for the 8-position. After deblocking the α-amino group at the N-terminal using trifluoroacetic acid (TFA), acetylation is achieved using a large excess of acetic anhydride in dichloromethane.

Following completion of the assembly of the peptide and acetylation of the N-terminus, the following intermediate is present: Ac-β-D-2NAL-(4Cl)D-Phe-D-3PAL-Ser(Bzl)-Lys-(Fmoc)-D-Lys(Fmoc)-Leu-Lys(Ipr)-Pro-D-Ala-NH-[MBHA resin support]. The unnatural amino acids in the 5- and 6-positions are formed by simultaneously carrying out the following reactions with the deprotected side chains of the Lys residues. The Fmoc protecting group is removed from both by treatment of the peptidoresin with 20 percent piperidine in DMF for 5 minutes, then washing with DMF, then treatment with more piperidine/DMF for 20 minutes. After washing the resin with DMF, $CH_3OH$ and finally DMF, the newly freed amino group is treated with a large excess (>10 fold) of diphenyl cyanocarbonimidate (PCI) in DMF. Thereafter, the peptide is then subjected to the standard wash (see Steps 10–11) and then treated with isopropylamine dissolved in DMF for 24 hours at about 22° C. to complete the formation of the aminoisopropyl cyanoguanidino moiety; for some of the more hindered reactants, this step may be repeated.

The cleavage of the peptide from the resin and deprotection of the Ser side chain takes place very readily at 0° C. with HF. Anisole is added as a scavenger prior to HF treatment. After the removal of HF under vacuum, the resin is extracted with 50% acetic acid, and the washings are lyophilized to provide a crude peptide powder.

Purification of the peptide is then effected by high performance liquid chromatography (HPLC), as known in the art and specifically set forth in J. Rivier, et al. *J. Chromatography*, 288 (1984) 303–328.

The peptide is judged to be homogeneous using thin layer chromatography and several different solvent systems, as well as by using reversed-phase high pressure liquid chromatography and an aqueous triethylammonium phosphate solution plus acetonitrile. Amino acid analysis of the resultant, purified peptide is consistent with the formula for the prepared structure, showing substantially integer-values for each amino acid in the chain; mass spectral analysis is also consistent. The optical rotation is measured on a photoelectric polarimeter as $[\alpha]_D^{20} = -2.8 \pm 0.5 (c=1, 50\%$ acetic acid).

The other peptides in Table I are similarly synthesized and purified. The peptides are assayed in vivo and may also be tested in vitro. If performed, in vitro testing is carried out using dissociated rat pituitary cells maintained in culture for 4 days prior to the assay. The levels of LH mediated in response to the application of peptides is assayed by specific radioimmunoassay for rat LH. Control dishes of cells only receive a measure which is 3 nanomolar in GnRH; experimental dishes receive a measure 3 nanomolar in GnRH plus a measure having either the present standard antagonist for comparison purposes i e [Ac-dehydro Pro$^1$, (4F)D-Phe$^2$, D-Trp$^{3,6}$]-GnRH or the test peptide, in concentrations ranging from 0.01 to 10 nanomolar. The amount of LH secreted in the samples treated only with GnRH is compared with that secreted by the samples treated with the peptide plus GnRH. The ability of the test peptide to reduce the amount of LH released by 3 nanomolar GnRH is compared to that of the present standard peptide.

The in vivo testing determines effectiveness to prevent ovulation in female rats. In this test, a specified number of mature female Sprague-Dawley rats, e.g. five to ten, each having a body weight from 225 to 250 grams, is injected with a specified microgram dosage of peptide in either saline, bacteriostatic water, polyethylene glycol, corn oil or mixtures of the above with ethanol at about noon on the day of proestrus. Proestrus is the afternoon of ovulation. A separate female rat group is used as a control to which the peptide is not administered. Each of the control female rats ovulates on the evening of proestrus; of the rats treated, the number of them which ovulate is recorded. Each of the peptides is considered to be totally effective to prevent ovulation of female rats at a dose of about 500 micrograms.

All peptides listed in Table I are considered effective to block GnRH-induced LH secretion in vitro at some reasonable concentration. All of the peptides are considered to be effective to prevent ovulation of female mammals at low dosages. The following Table A shows the results of in vivo testing of various of these GnRH antagonists with the dosages being given in micrograms:

TABLE A

| Peptide No. | Dosage | Rats Ovulating | Dosage | Rats Ovulating |
|---|---|---|---|---|
| 1. | 2.5 | 0/9 | 1.0 | 0/5 |
| 2. | 2.5 | 6/6 | 2.0 | 2/10 |
| 3. | 2.5 | 7/9 | 2.0 | 1/10 |
| 4. | 2.5 | 0/6 | 2.0 | 1/10 |
| 5. | 2.0 | 1/10 | | |
| 6. | 2.5 | 0/6 | 1.0 | 7/17 |
| 7. | 2.5 | 3/20 | | |

TABLE A-continued

| Peptide No. | Dosage | Rats Ovulating | Dosage | Rats Ovulating |
|---|---|---|---|---|
| 8. | 2.5 | 5/19 | 1.0 | 5/5 |
| 9. | 2.5 | 0/6 | 1.0 | 5/5 |
| 10. | 2.5 | 5/8 | 2.0 | 1/10 |
| 12. | 2.5 | 6/7 | 5.0 | 9/10 |
| 13. | 5.0 | 5/12 | 10.0 | 3/5 |
| 15. | 2.5 | 0/4 | 1.0 | 8/18 |

EXAMPLE II

Peptides as indicated in TABLE II having the formula: Ac-dehydroPro-(A)D-Phe-AA$_3$-Ser-AA$_5$-β-D-2NAL-Leu-AA$_8$-Pro-D-Ala-NH$_2$ are prepared by the solid-phase procedure referred to above.

TABLE II

| | A | AA$_3$ | AA$_5$ | AA$_8$ |
|---|---|---|---|---|
| 17 | 4Cl | β-D-2NAL | Tyr | Lys(bcg) |
| 18 | " | " | " | Lys(ecg) |
| 19 | 4F | (1For)D-Trp | (2F)Phe | Orn(ecg) |
| 20 | " | " | Tyr | Dpr(2ncg) |
| 21 | " | " | (2NO$_2$)Phe | Dbu(icg) |
| 22 | " | (1Ac)D-Trp | (2CH$_3$)Phe | Dbu(2mpcg) |
| 23 | 4Br | " | Tyr | Dbu(3mpcg) |
| 24 | " | " | (2Br)Phe | Dbu(4mpcg) |
| 25 | H | D-Trp | (2Cl)Phe | Orn(2mncg) |
| 26 | 4NO$_2$ | (5CH$_3$)D-Trp | (3CH$_3$)Phe | Orn(hcg) |
| 27 | " | (5F)D-Trp | His | Lys(tcg) |
| 28 | 2,4Cl$_2$ | (5Cl)D-Trp | (3F)Phe | Dpr(trcg) |
| 29 | " | (6NO$_2$)D-Trp | (3Br)Phe | Orn(1ncg) |
| 30 | C$^\alpha$Me/4Cl | (5OCH$_3$)D-Trp | (3I)Tyr | Orn(pcg) |
| 31 | 3,4Cl$_2$ | (5NH$_2$)D-Trp | (3Cl)Phe | Dpr(chcg) |

All peptides listed in Table II are considered effective to block GnRH-induced LH secretion in vitro at some reasonable concentration. All of the peptides are considered to be effective to prevent ovulation of female mammals at low dosages.

EXAMPLE III

Peptides as indicated in TABLE III having the formula: G-β-D-2NAL-(4Cl)D-Phe-D-3PAL-Ser-Tyr-AA$_6$-Leu-AA$_8$-Pro-AA$_{10}$ are prepared by the solid-phase procedure referred to above.

TABLE III

| | G | AA$_6$ | AA$_8$ | AA$_{10}$ |
|---|---|---|---|---|
| 32 | Ac | D-Arg | Lys(bcg) | D-Ala—NH$_2$ |
| 32A | Ac | D-Arg | Lys(tcg) | D-Ala—NH$_2$ |
| 33 | Ac | D-Lys(bcg) | Arg | " |
| 34 | For | D-Tyr | Lys(icg) | Gly—NH$_2$ |
| 35 | Bz | (Et)D-Arg | Orn(icg) | " |
| 36 | Ac | D-Lys | Orn(ecg) | " |
| 37 | Vac | D-Har | Orn(mcg) | " |
| 38 | Acr | (4gua)D-Phe | Dpr(2ncg) | AzaGly—NH$_2$ |
| 39 | Ac | D-Orn | Dpr(chcg) | D-Ala—NH$_2$ |
| 40 | Acr | D-His | Dpr(tcg) | " |
| 41 | Ac | (Bu)D-Arg | Dbu(1mncg) | " |
| 42 | " | (Bz)D-Orn | Dbu(2mpcg) | " |
| 43 | Vac | (4NH$_2$)D-Phe | Dbu(4mpcg) | " |
| 44 | Bz | (Ac)D-Lys | Dbu(trcg) | AzaGly—NH$_2$ |

All peptides listed in Table III are considered effective to block GnRH-induced LH secretion in vitro at some reasonable concentration. All of the peptides are considered to be effective to prevent ovulation of female mammals at low dosages.

EXAMPLE IV

Peptides as indicated in TABLE IV having the formula: Ac-$AA_1$-(4Cl)D-Phe-D-3PAL-Ser-Tyr-D-Arg-$AA_7$-$AA_8$-Pro-D-Ala-$NH_2$ are prepared by the solid-phase procedure referred to above.

TABLE IV

| | $AA_1$ | $AA_7$ | $AA_8$ |
|---|---|---|---|
| 45 | β-D-2NAL | Leu | Lys(bcg) |
| 46 | (1Ac)D-Trp | Met | Lys(2mpcg) |
| 47 | (6Br)D-Trp | Tyr | Lys(3mpcg) |
| 48 | (5F)D-Trp | Nle | Lys(4mpcg) |
| 49 | ($6NO_2$)D-Trp | Met | Orn(chcg) |
| 50 | (5Cl)D-Trp | Tyr | Orn(pcg) |
| 51 | (4Cl)D-Phe | Phe | Dpr(pcg) |
| 52 | (4F)D-Phe | (4F)Phe | Dpr(tcg) |
| 53 | (2,4$Cl_2$)D-Phe | NML | Dbu(mcg) |
| 54 | dehydroPro | Nle | Dbu(2ncg) |
| 55 | β-D-2NAL | Leu | Lys(Ocg) |
| 56 | ($6OCH_3$)D-Trp | (1For)Trp | Orn(1ncg) |
| 57 | ($5NH_2$)D-Trp | Nva | Orn(ecg) |
| 58 | ($4NO_2$)D-Phe | NML | Orn(1mncg) |
| 59 | dehydroPro | ($6NO_2$)Trp | Dbu(hicg) |

All peptides listed in Table IV are considered effective to block GnRH-induced LH secretion in vitro at some reasonable concentration. All of the peptides are considered to be effective to prevent ovulation of female mammals at low dosages.

EXAMPLE V

Peptides as indicated in TABLE V having the formula: Ac-$AA_1$-(4Cl)D-Phe-$AA_3$-Ser-$AA_5$-$AA_6$-Leu-ILys-Pro-D-Ala-$NH_2$ are prepared by the solid-phase procedure referred to above.

TABLE V

| | $AA_1$ | $AA_3$ | $AA_5$ | $AA_6$ |
|---|---|---|---|---|
| 60 | β-D-2NAL | D-3PAL | Lys(bcg) | β-D-2NAL |
| 61 | " | ($6NO_2$)D-Trp | " | (Dnp)D-His |
| 62 | " | D-Trp | Lys(ecg) | (4gua)D-Phe |
| 63 | dehydroPro | β-D-2NAL | Orn(ecg) | ($6NO_2$)D-Trp |
| 64 | " | β-D-1NAL | Orn(mcg) | D-Val |
| 65 | β-D-2NAL | (1For)D-Trp | Orn(tcg) | (Pr)D-Arg |
| 66 | " | " | Dbu(bcg) | ($5NH_2$)D-Trp |
| 67 | dehydroPro | D-Trp | Dbu(2mpcg) | D-Tyr |
| 68 | " | D-2PAL | Dbu(4mpcg) | D-Nle |
| 69 | " | (1Ac)D-Trp | Dbu(hcg) | (4F)D-Phe |
| 70 | Pro | D-3PAL | Lys(pcg) | β-D-1NAL |
| 71 | (1For)D-Trp | " | Lys(chcg) | ($4NHCH_3$)D-Phe |
| 72 | β-D-2NAL | " | Dpr(hcg) | (Ac)D-Orn |
| 73 | " | " | Dpr(Ocg) | ($4NH_2$)D-Phe |
| 74 | β-D-1NAL | (6Br)D-Trp | Dpr(tcg) | (1For)D-Trp |
| 75 | ($6CH_3$)D-Trp | D-4PAL | Dpr(bzcg) | D-4PAL |

The peptides listed in Table V are considered effective to block GnRH-induced LH secretion in vitro at a reasonable concentration. All of the peptides are considered to be effective to prevent ovulation of female mammals at low dosages.

EXAMPLE VI

Peptides as indicated in TABLE VI having the formula: G-$AA_1$-(4Cl)D-Phe-D-Trp-Ser-Tyr-$AA_6$-Leu-$AA_8$-Pro-D-Ala-$NH_2$ are prepared by the solid-phase procedure referred to above.

TABLE VI

| | G | $AA_1$ | $AA_6$ | $AA_8$ |
|---|---|---|---|---|
| 76 | Ac | dehydroPro | D-Lys(bcg) | Lys(bcg) |
| 77 | Ac | β-D-2NAL | β-D-2NAL | Lys(3mpcg) |
| 78 | Ac | β-D-2NAL | D-Val | Lys(tcg) |
| 79 | Acr | Pro | D-Ser(OtBu) | Lys(chcg) |
| 80 | H | dehydroPro | (imBzl)D-His | Lys(ecg) |
| 81 | Bz | (4Br)D-Phe | (5Cl)D-Trp | Orn(ecg) |
| 82 | " | " | D-pGlu | (6Br)D-Trp | Orn(bzcg) |
| 83 | For | β-D-1NAL | (Me)D-Arg | Orn(Ocg) |
| 84 | " | dehydroPro | D-Har | Orn(4mpcg) |
| 85 | Vac | β-D-2NAL | (Bz)D-Lys | Orn(chcg) |
| 86 | Ac | β-D-($Arg^5$) | β-D-2NAL | Lys(Ocg) |
| 87 | H | dehydroPro | D-Ala | Lys(tcg) |

The peptides listed in Table VI are considered effective to block GnRH-induced LH secretion in vitro at a reasonable concentration. All of the peptides are considered to be effective to prevent ovulation of female mammals at low dosages.

EXAMPLE VII

Peptides as indicated in TABLE VII having the formula: Ac-β-D-2NAL-(4Cl)D-Phe-D-3PAL-Ser-$AA_5$-$AA_6$-Leu-$AA_8$-Pro-D-Ala-$NH_2$ are prepared by the solid-phase procedure referred to above.

TABLE VII

| | $AA_5$ | $AA_6$ | $AA_8$ |
|---|---|---|---|
| 88 | Arg | D-Lys(bcg) | Arg |
| 89 | " | D-Lys(Ocg) | " |
| 90 | Orn(bcg) | (4gua)D-Phe | ($Et_2$)Arg |
| 91 | Lys(2ncg) | D-Lys(2ncg) | ILys |
| 92 | Orn(bzcg) | D-Lys(bzcg) | Har |
| 93 | Lys(act) | D-Lys(act) | ILys |
| 94 | Lys(hicg) | D-Lys(hicg) | ILys |
| 95 | Lys(trcg) | D-Lys(trcg) | ILys |
| 96 | Lys(bcg) | D-Lys(bcg) | ILys |
| 97 | " | D-3PAL | (EtPr)Har |
| 98 | " | D-Lys(Nic) | ($Me_2$)Arg |
| 99 | Orn(tcg) | D-Lys(tcg) | (MeBu)Arg |
| 100 | Lys(Sbcg) | D-Lys(Sbcg) | ILys |

The peptides listed in Table VII are considered effective to block GnRH-induced LH secretion in vitro at a reasonable concentration. All of the peptides are considered to be effective to prevent ovulation of female mammals at low dosages.

EXAMPLE VIII

Peptides as indicated in TABLE VIII having the formula: Ac-β-D-2NAL-(4Cl)D-Phe-D-3PAL-Ser-$AA_5$-$AA_6$-Leu-$AA_8$-Pro-D-Ala-$NH_2$ are prepared by the solid-phase procedure referred to above.

TABLE VIII

| | $AA_5$ | $AA_6$ | $AA_8$ |
|---|---|---|---|
| 101 | Orn(bcg) | D-Orn(bcg) | ILys |
| 101A | Lys(bcg) | D-Lys(bcg) | ILys |
| 102 | Orn(2mpcg) | D-Orn(2mpcg) | ILys |
| 103 | Orn(tcg) | D-Orn(tcg) | ILys |
| 103A | Aph(tcg) | D-Aph(tcg) | ILys |
| 103B | Lys(tcg) | D-Lys(tcg) | ILys |
| 104 | Orn(bcg) | β-D-2NAL | ILys |

TABLE VIII-continued

|      | AA₅        | AA₆         | AA₈       |
|------|------------|-------------|-----------|
| 104A | Aph(bcg)   | D-Aph(bcg)  | ILys      |
| 105  | Orn(2mpcg) | β-D-2NAL    | ILys      |
| 105A | Lys(Nic)   | D-Lys(Nic)  | Lys(tcg)  |
| 106  | Lys(Nic)   | D-Lys(Nic)  | Lys(bur)  |
| 106A | Lys(tcg)   | D-Lys(Nic)  | ILys      |
| 106B | Lys(Nic)   | D-Lys(tcg)  | ILys      |
| 107  | Lys(2ncg)  | D-Lys(2ncg) | ILys      |
| 108  | Lys(bzcg)  | D-Lys(bzcg) | ILys      |
| 109  | Lys(icg)   | D-Lys(icg)  | Arg       |
| 110  | Orn(icg)   | D-Orn(icg)  | ILys      |

As a further working example, a solid phase synthesis is set forth hereinafter of peptide No. 103A above, which is referred to as [Ac-β-D-2NAL$^1$, (4Cl)D-Phe$^2$, D-3PAL$^3$, Aph(tcg)$^5$, D-Aph(tcg)$^6$, ILys$^8$, D-Ala$^{10}$]-GnRH. This peptide has the following formula:
Ac-β-D-2NAL-(4Cl)D-phe-D-3PAL-Ser-Aph(3-amino 1,2,4 triazole)-D-Aph (3-amino 1,2,4 triazole)-Leu-Lys (isopropyl)-Pro-D-Ala-NH$_2$.

An MBHA resin is used, and Boc-protected D-Ala is coupled to the resin over a 2-hour period in CH$_2$Cl$_2$ using a 3-fold excess of Boc derivative and DCC as an activating reagent. The D-Ala residue attaches to the MBHA resin by an amide bond.

Following the coupling of each amino acid residue, washing, deblocking and coupling of the next amino acid residue is carried out in accordance with the schedule set forth hereinbefore, using an automated machine and beginning with about 5 grams of resin. The side chain primary amino groups of Aph in the 5-position and of D-Aph in the 6-position are protected by Fmoc. Bzl(benzyl ether) is used as a side chain protecting group for the hydroxyl group of Ser. Boc-Lys(Ipr,Z) is used for the 8-position. After deblocking the α-amino group at the N-terminus using trifluoroacetic acid (TFA), acetylation is achieved using a large excess of acetic anhydride in dichloromethane.

Following completion of the assembly of the peptide and acetylation of the N-terminus, the following intermediate is present: Ac-β-D-2NAL-(4Cl)D-Phe-D-3PAL-Ser(Bzl)-Aph(Fmoc)-D-Aph(Fmoc)-Leu-Lys(Ipr,Z)-Pro-D-Ala-NH-[MBHA resin support]. The unnatural amino acids in the 5- and 6-positions are formed by simultaneously carrying out the following reactions with the deprotected side chains of the Aph residues. The Fmoc protecting group is removed from both by treatment of the peptidoresin with 20 percent piperidine in DMF for 5 minutes, then washing with DMF, then treatment with more piperidine/DMF for 20 minutes. After washing the resin with DMF, CH$_3$OH and finally DMF, the newly freed amino group is treated with a large excess (>10 fold) of diphenyl cyanocarbonimidate(PCI) in DMF. Thereafter, the peptide is then subjected to the standard wash and then treated with hydrazine, dissolved in DMF, for 24 hours at about 22° C. to complete the formation of the cyanoguanidino moiety; this step is preferably repeated. The cyanoguanidino moieties that are formed spontaneously convert to the corresponding heterocycle, i.e. 3-amino, 1,2,4 triazole. The formation of the triazole moieties can take place anytime after the peptide chain has been elongated to include the 5-position residue, and there may be an advantage in forming these moieties prior to adding D-3PAL to avoid the possibility of potential side reactions.

The cleavage of the peptide from the resin and deprotection of the Ser and the Lys side chains takes place very readily at 0° C. with HF. Anisole is added as a scavenger prior to HF treatment. After the removal of HF under vacuum, the resin is extracted with 5% acetic acid, and the washings are lyophilized to provide a crude peptide powder.

Purification of the peptide is then effected by high performance liquid chromatography (HPLC), as known in the art and specifically set forth in J. Rivier, et al. *J. Chromatography*, 288 (1984) 303–328.

The peptide is judged to be homogeneous using capillary zone electrophoresis (CZE), as well as by using reversed-phase high performance liquid chromatography and an aqueous triethylammonium phosphate solution plus acetonitrile. Amino acid analysis of the resultant, purified peptide is consistent with the formula for the prepared structure, showing substantially integer-values for each amino acid in the chain; mass spectral analysis is also consistent. The optical rotation is measured on a photoelectric polarimeter as $$[\alpha]_D^{20} = -33 \pm 1.0 (c=1, 50\% \text{ acetic acid}).$$

In addition to the above synthesis, Peptide 103A is also synthesized with glycinamide at the C-terminus instead of D-Ala-NH$_2$; biological testing in vivo shows it is slightly less biologically potent than Peptide 103A.

Peptide 103A was also synthesized with the N-ethylamide at the C-terminus instead of D-Ala-NH$_2$; biological testing in vivo showed it exhibited just slightly less biological potency than that reported in TABLE B for Peptide 103B. In addition, Peptide 104A is also synthesized with the glycinamide at the C-terminus instead of D-Ala-NH$_2$; biological testing in vivo shows somewhat less biological potency than that reported in TABLE B for Peptide 104A.

All peptides listed in Table VIII are considered effective to block GnRH-induced LH secretion in vitro at some reasonable concentration. All of the peptides are considered to be effective to prevent ovulation of female mammals at low dosages.

In addition to the in vivo testing, mentioned above, to determine effectiveness to prevent ovulation in female rats, groups of about 6 adult castrate male Sprague-Dawley rats, each having a body weight from 225 to 250 grams, are each injected IV with a 50 microgram dosage of either Peptide No. 103A or a standard antagonist referred to as the Nal-Glu antagonist (see *J. Clin. Edno. Metab.*, 71, 4, 881–888 (1990)) in either corn oil or a phosphate buffer in the presence of BSA (bovine serum albumin). A separate rat group is used as a control, to which only the carrier is administered. Each of the control rats and the rats being treated are monitored for LH levels in the bloodstream at about 3 hours, 24 hours, 36 hours and 48 hours following this single bolus injection. Peptide No. 103A is surprisingly effective to suppress the level of circulating LH in the bloodstream of male rats, at levels very substantially below that of the control and, after 12 hours, below that of the rats treated with the Nal-Glu antagonist. This very long-acting duration of biological effect was truly surprising.

EXAMPLE IX

Peptides as indicated in TABLE IX having the formula: Ac-β-D-2NAL-(4Cl)D-Phe-AA$_3$-Ser-AA$_5$-AA$_6$-Leu-AA$_8$-Pro-D-Ala-NH$_2$ are prepared by the solid-phase procedure referred to above.

TABLE IX

|      | AA₃        | AA₅ | AA₆    | AA₈  |
|------|------------|-----|--------|------|
| 111  | D-Lys(bcg) | Tyr | D-Arg  | Arg  |
| 111A | D-Aph(icg) | Tyr | D-3PAL | ILys |

TABLE IX-continued

|  | $AA_3$ | $AA_5$ | $AA_6$ | $AA_8$ |
|---|---|---|---|---|
| 112 | D-Lys(2mpcg) | Tyr | D-Arg | Arg |
| 113 | D-Lys(tcg) | Tyr | D-Arg | Arg |
| 113A | D-Lys(tcg) | Tyr | D-Lys(tcg) | ILys |
| 114 | D-Lys(bcg) | Arg | β-D-2NAL | Arg |
| 114A | D-Lys(2mpcg) | Arg | β-D-2NAL | Arg |
| 115 | D-Lys(tcg) | Arg | β-D-2NAL | Arg |
| 116 | D-Lys(bcg) | Tyr | D-Arg | ILys |
| 117 | D-Lys(tcg) | Tyr | D-Arg | ILys |
| 117A | D-Lys(tcg) | Tyr | D-3PAL | Arg |
| 117B | D-Aph(tcg) | Tyr | D-3PAL | ILys |
| 118 | D-Lys(bcg) | Tyr | β-D-2NAL | ILys |
| 119 | D-Lys(tcg) | Tyr | D-3PAL | ILys |
| 119A | D-Aph(bcg) | Tyr | D-3PAL | ILys |
| 120 | D-Lys(2mpcg) | Tyr | D-3PAL | ILys |
| 120A | D-Lys(2mpcg) | Arg | β-D-2NAL | Arg |
| 121 | D-Lys(bcg) | Tyr | D-Arg | Arg |
| 122 | D-Lys(bcg) | Lys(bcg) | D-Lys(bcg) | ILys |
| 122A | D-Lys(bcg) | Tyr | D-Lys(bcg) | ILys |
| 123 | D-3PAL | Lys(bur) | β-D-2NAL | Arg |
| 124 | D-Lys(bcg) | Tyr | β-D-2NAL | Lys(bcg) |
| 125 | D-Orn(2mpcg) | Tyr | β-D-2NAL | ILys |
| 125A | D-Orn(tcg) | Tyr | D-3PAL | ILys |
| 125B | D-Orn(bcg) | Tyr | D-3PAL | ILys |

All peptides listed in Table IX are considered effective to block GnRH-induced LH secretion in vitro at some reasonable concentration. All of the peptides are considered to be effective to prevent ovulation of female mammals at low dosages.

EXAMPLE X

Peptides as indicated in TABLE X having the formula: Ac-β-D-2NAL-(4Cl)D-Phe-D-3PAL-Ser-$AA_5$-$AA_6$-$AA_7$-ILy-Pro-$AA_{10}$ are prepared by the solid-phase procedure referred to above.

TABLE X

|  | $AA_5$ | $AA_6$ | $AA_7$ | $AA_{10}$ |
|---|---|---|---|---|
| 125C | Aph(tcg) | D-Aph(tcg) | NML | D-Ala—$NH_2$ |
| 125D | Aph(tcg) | D-Aph(tcg) | Leu | $NHCH_2CH_3$ |
| 125E | Aph(tcg) | D-Aph(tcg) | NML | " |
| 125F | Aph(tcg) | D-Aph(tcg) | Leu | Gly—$NH_2$ |
| 125G | Aph(2mpcg) | D-Aph(2mpcg) | NML | D-Ala—$NH_2$ |

The peptides listed in Table X are considered effective to block GnRH-induced LH secretion in vitro at a reasonable concentration. All of the peptides are considered to be effective to prevent ovulation of female mammals at low dosages.

Results of in vivo testing of selected of these antagonists are shown in the following Table B, with the dosages being given in micrograms:

TABLE B

| Peptide No. | Dosage | Rats Ovulating | Dosage | Rats Ovulating |
|---|---|---|---|---|
| 17. | 10 | 6/8 | 15 | 7/10 |
| 32A. | 10 | 0/6 | 5 | 0/6 |
|  | 2.5 | 0/7 | 1.0 | 5/10 |
| 33. | 2.5 | 4/17 | | |
| 55. | 10 | 6/7 | 25 | 2/5 |
| 60. | 2.5 | 4/14 | 1.0 | 8/10 |
| 86. | 2.5 | 4/15 | 5.0 | 5/5 |
| 88. | 2.5 | 0/4 | 1.0 | 4/15 |
|  | 10 | 0/8 | | |
| 89. | 10 | 2/18 | | |
| 93. | 2.5 | 5/10 | | |
| 94. | 1.0 | 7/11 | | |
| 96. | 1.0 | 9/12 | | |
| 101. | 2.5 | 0/5 | 1.0 | 5/8 |
| 102. | 2.5 | 2/9 | | |
| 103. | 2.5 | 5/7 | | |
| 103A. | 2.5 | 0/8 | 1.0 | 0/7 |
|  |  |  | 0.5 | 7/8 |
| 103B. | 2.5 | 0/7 | 1.0 | 3/9 |
|  |  |  | 0.5 | 7/8 |
| 104. | 2.5 | 6/8 | | |
| 104A. | 5.0 | 6/11 | 2.5 | 2/3 |
| 105. | 2.5 | 0/5 | | |
| 105A. | 5.0 | 4/6 | | |
| 106. | 5.0 | 0/7 | | |
| 106A. | 2.0 | 0/5 | 1.0 | 7/7 |
| 106B. | 2.5 | 0/6 | 1.0 | 4/6 |
| 111. | 2.5 | 1/11 | 1.0 | 0/5 |
|  |  |  | 0.5 | 5/7 |
| 111A. | 15 | 0/9 | 5 | 2/4 |
| 112. | 1.0 | 4/8 | | |
| 113. | 1.0 | 5/6 | | |
| 113A. | 5.0 | 0/6 | 2.5 | 1/15 |
| 114. | 5.0 | 4/5 | | |
| 115. | 2.5 | 2/8 | | |
| 116. | 2.5 | 0/6 | 1.0 | 2/8 |
| 117. | 10 | 0/6 | 5 | 2/5 |
| 117A. | 2.5 | 0/7 | 1.0 | 4/9 |
| 117B. | 15 | 1/5 | | |
| 118. | 15 | 4/5 | 5 | 5/5 |
| 119. | 2.5 | 0/7 | 1.0 | 2/10 |
| 119A. | 15 | 4/6 | | |
| 120. | 2.5 | 0/8 | 1.0 | 6/7 |
| 120A. | 5.0 | 4/6 | | |
| 122. | 10 | 4/6 | | |
| 122A. | 5.0 | 0/6 | 2.5 | 5/6 |
| 123. | 10 | 1/10 | 5 | 0/6 |
| 125. | 2.5 | 3/7 | | |
| 125A. | 5.0 | 1/8 | 2.5 | 1/7 |
| 125B. | 2.5 | 0/7 | | |
| 125C. | 1.0 | 0/8 | 0.5 | 6/10 |
| 125D. | 2.5 | 0/8 | 1.0 | 8/9 |
| 125E. | 10 | 0/5 | | |
| 125F. | 1.0 | 9/16 | | |
| 125G. | 5.0 | 0/6 | | |

EXAMPLE XI

Peptides as indicated in TABLE XI having the formula: pGlu-His-Trp-Ser-Tyr-$AA_6$-$AA_7$-Arg-Pro-$AA_{10}$ are prepared by the solid phase procedure referred to above.

TABLE XI

|  | $AA_6$ | $AA_7$ | $AA_{10}$ |
|---|---|---|---|
| 126 | D-Lys(bcg) | Leu | Gly—$NH_2$ |
| 126A | D-Aph(bcg) | " | " |
| 127 | D-Lys(ecg) | " | " |
| 128 | D-Lys(pcg) | " | " |
| 129 | D-Lys(hcg) | " | AzaGly—$NH_2$ |
| 130 | D-Lys(tcg) | " | $NHCH_2CH_3$ |
| 130A | D-Aph(tcg) | " | " |
| 131 | D-Lys(4mpcg) | " | " |
| 132 | D-Lys(3mpcg) | NML | " |
| 133 | D-Lys(2mpcg) | " | " |
| 134 | D-Lys(chcg) | Leu | Gly—$NH_2$ |
| 134A | D-Aph(tcg) | " | " |
| 135 | D-Lys(Ocg) | " | " |
| 136 | D-Orn(bcg) | " | " |
| 137 | D-Orn(tcg) | NML | AzaGly$NH_2$ |
| 138 | D-Orn(mcg) | " | $NHCH_2CH_3$ |

TABLE XI-continued

| | AA$_6$ | AA$_7$ | AA$_{10}$ |
|---|---|---|---|
| 139 | D-Dbu(2mpcg) | " | NHCH$_3$ |
| 140 | D-Dbu(chcg) | Leu | NHCH$_2$CH$_2$CH$_3$ |
| 141 | D-Dbu(bzcg) | " | Gly—NH$_2$ |
| 142 | D-Dpr(ecg) | " | " |
| 143 | D-Dpr(hicg) | NML | " |
| 144 | D-Dpr(trcg) | " | NHCH$_2$CH$_3$ |

The peptides described in TABLE XI are considered to be effective to cause the release of LH and FSH in female rats. All of them are considered to be substantial more effective than native GnRH.

An exemplary synthesis of Peptide No. 130A which has the formula pGlu-His-Trp-Ser-Tyr-D-Aph(3-amino-1,2,4-triazole)-Leu-Arg-Pro-NHCH$_2$CH$_3$ is set forth hereinafter.

An N-ethylamino methyl resin is used, and Boc-protected Pro is coupled to the resin over a 2-hour period in CH$_2$Cl$_2$ using a 3-fold excess of Boc derivative and DCC as an activating reagent. The Pro residue attaches by an amide bond to the secondary amino group on the resin.

Following the coupling of each amino acid residue, washing, deblocking and coupling of the next amino acid residue is carried out in accordance with the schedule set forth hereinbefore, using an automated machine and beginning with about 5 grams of resin. The side chain primary amino group of D-Aph in the 6-position is protected by Fmoc. Bzl(benzyl ether) is used as a side chain protecting group for the hydroxyl group of Ser, and 2,6-dichlorobenzyl is used as the side chain protecting group for the hydroxyl group of Tyr. Boc-Arg(Tos) is used for the 8-position, and Boc-His(Tos) is used for the 2-position. pGlu at the N-terminus is introduced as Z-pGlu or as plain pGlu, as desired.

Following completion of the assembly of the peptide, the following intermediate is present: pGlu-His(Tos)-Trp-Ser-(Bzl)-Tyr(DCB)-D-Aph(Fmoc)-Leu-Arg(Tos)-Pro-N(Et)-[resin support]. The unnatural amino acid in the 6-position is formed by carrying out the following reactions with the deprotected side chain of the D-Aph residue. The Fmoc protecting group is removed by treatment of the peptidoresin with 20 percent piperidine in DMF for 5 minutes, then washing with DMF, then treatment with more piperidine/DMF for 20 minutes. After washing the resin with DMF, CH$_3$OH, CH$_2$Cl$_2$, and finally DMF, the newly freed amino group is treated with a large excess (>10 fold) of diphenyl cyanocarbonimidate(PCI) in DMF. Thereafter, the peptide is then subjected to the standard wash and then treated with hydrazine, dissolved in DMF, for 24 hours at about 22° C. to complete the formation of the cyanoguanidino moiety; this step is preferably repeated. The cyanoguanidino moieties that are formed spontaneously convert to the corresponding heterocycle, i.e. 3-amino, 1,2,4 triazole.

The cleavage of the peptide from the resin and deprotection of the pGlu, His, Ser, Tyr and Arg side chains takes place very readily at 0° C. with HF. Anisole is added as a scavenger prior to HF treatment. After the removal of HF under vacuum, the resin is extracted with 50% acetic acid, and the washings are lyophilized to provide a crude peptide powder.

Purification of the peptide is then effected by high performance liquid chromatography (HPLC), as known in the art and specifically set forth in J. Rivier, et al. *J. Chromatography*, 288 (1984) 303–328.

The peptide is judged to be homogeneous using capillary zone electrophoresis (CZE), as well as by using reversed-phase high performance liquid chromatography and an aqueous triethylammonium phosphate solution plus acetonitrile. Amino acid analysis of the resultant, purified peptide is consistent with the formula for the prepared structure, showing substantially integer-values for each amino acid in the chain; mass spectral analysis is also consistent.

In addition to the above synthesis, Peptide 134A is also synthesized with glycinamide at the C-terminus instead of the ethylamide; biological testing in vivo shows it is just slightly less biologically potent than Peptide 130A.

EXAMPLE XII

A peptide intermediate having the formula: Ac-β-D-2NAL-(4Cl)D-Phe-D-3PAL-Ser(Bzl)-Lys(Fmoc)-D-3PAL-NML-Lys(Dts)-Pro-D-Ala-NH-[resin support] is prepared by the solid phase procedure generally referred to above. The intermediate is then treated with piperidine to remove the Fmoc protecting group and is thereafter reacted with PCI as hereinbefore described. Next the Dts protecting group is removed from the amino side chain of the Lys residue in the 8-position using a suitable thiol, such as β-mercaptoethanol or thiophenol(PhSH), in DMF, and the peptidoresin is given the standard wash. Thereafter, it is maintained at 22° C. for 10–60 minutes or until the ninhydrin test is negative to allow the reaction to proceed to completion, effecting cyclization of the side-chain primary amino group of Lys$^8$ and the cyanoguanidino moiety which was earlier formed upon the Lys$^5$ side chain. Deprotection and cleavage are then carried out as previously described. Following HPLC purification as previously described, the GnRH antagonist (Peptide No. 145) is tested. The peptide is considered to be effective to prevent ovulation of female mammals at low dosages.

EXAMPLE XIII

A peptide intermediate having the formula: Ac-β-D-2NAL-(4Cl)D-Phe-D-3PAL-Ser(Bzl)-Orn(Fmoc)-D-Trp-Leu-Lys(Nps)-Pro-D-Ala-NH-[resin support] is prepared by the solid phase procedure referred to above. The peptide intermediate is treated with a suitable thiol as described in Example 145 to form the cyanoguanidino moiety by reaction of PCI with the side chain amino group of the Lys residue in the 8-position, and it is then cyclized with the deprotected side chain amino group of Orn in the 5-position following removal of the Fmoc protecting group. Following cleavage and HPLC purification as previously described, the GnRH antagonist (Peptide No. 146) is tested. The peptide is considered to be effective to prevent ovulation of female mammals at low dosages.

EXAMPLE XIV

A peptide intermediate having the formula: Ac-β-D-2NAL-(4Cl)D-Phe-D-3PAL-Ser(Bzl)-Tyr(2BrZ)-D-Lys(Fmoc)-Leu-Lys(Ipr)-Pro-D-Ala-NH-[resin support] is prepared by the solid phase procedure referred to above. Following the removal of the Fmoc protection, the peptide intermediate is reacted as generally described in Example I using naphthyl isocyanate instead of PCI to form the napthylurea moiety with the side chain amino group of the D-Lys residue in the 6-position. Following cleavage and HPLC purification as previously described, the GnRH antagonist (Peptide No. 147) is tested. The peptide is considered to be effective to prevent ovulation of female mammals at low dosages.

EXAMPLE XV

A peptide intermediate having the formula: Ac-β-D-2NAL-(4Cl)D-Phe-D-3PAL-Ser(Bzl)-Tyr(2BrZ)-D-Lys(Fmoc)-Leu-Lys(Ipr)-Pro-D-Ala-NH-[resin support] is prepared by the solid phase procedure referred to above. Following the removal of the Fmoc protection, the peptide intermediate is reacted as generally described in Example I using naphthyl isothiocyanate instead of PCI to form the napthylthiourea moiety with the side chain amino group of the residue in the 6-position. Following cleavage and HPLC purification as previously described, the GnRH antagonist (Peptide No. 148) is tested. The peptide is considered to be effective to prevent ovulation of female mammals at low dosages.

EXAMPLE XVI

A peptide intermediate having the formula: Ac-β-D-2NAL-(4Cl)D-Phe-D-3PAL-Ser(Bzl)-Tyr(2BrZ)-D-Lys(Fmoc)-Leu-Lys(Ipr)-Pro-D-Ala-NH-[resin support] is prepared by the solid phase procedure referred to above. Following the removal of the Fmoc protection, the peptide intermediate is first reacted using 2-bromoethyl,2'(Boc-amino)ethyl ether dissolved in DMF for 1 hour or until the ninhydrin test is negative to link the carbon atom to the side-chain amino group by the removal of the halogen to form: Q—NH—$(CH_2)_2$—O—$(CH_2)_2$—NH(Boc). This compound is then reacted as generally described in Example I using PCI to form the cyanoguanidino moiety with the side chain secondary amino group of the residue in the 6-position. Next the Boc protection group is removed, and the primary amino group reacts with the —OPh group to give the compound:

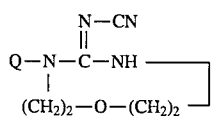

Following cleavage and HPLC purification as previously described, the GnRH antagonist (Peptide No. 149) is tested. The peptide is considered to be effective to prevent ovulation of female mammals at low dosages.

EXAMPLE XVII (Boc)Dpr is reacted with PCI as in Example I to produce

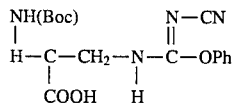

hydrazine dissolved in DMF for 1 to 2 days at room temperature, washed with DMF and then repeated to replace the —OPh group with concomminent formation of the heterocycle:

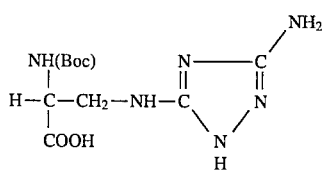

which is particularly useful as a substitute for His in peptide syntheses.

Following purification of the peptides, various of them are further characterized by subjection to high performance liquid chromatography on $C_{18}$ silica (Vydac 0.46×25 cm) using a flow rate of 1.7 ml/min and a gradient of from 35% to 85% by volume of Buffer B over a time span of 50 minutes, with the remainder being Buffer A. Buffer A is a solution of 0.3% triethylamine (v/v) and 0.1% phosphoric acid in water at pH 7.0; Buffer B is 60% by volume acetonitrile in Buffer A. The following Table C shows when the specific peptides elute from the $C_{18}$ silica having a particle size of about 5μ and a pore size of 300 Å when subjected to a gradient of from 35% Buffer B to 85% Buffer B (by volume with the remainder being Buffer A) over 50 minutes at a flow rate of 1.7 ml. per minute, and thereafter at 85% isocratically for 10 min.:

TABLE C

| Peptide No. | Time of Elution |
|---|---|
| 1. | |
| 2. | 26.56 |
| 3. | 47.6 |
| 4. | 20.32 |
| 5. | 35.6 |
| 6. | 31.04 |
| 7. | 28.96 |
| 8. | 27.74 |
| 9. | 54.24 |
| 10. | 30.86 |
| 11. | 56.9 |
| 12. | 46.78 |
| 13. | 33.4 |
| 15. | 41.1 |
| 17. | 49.6 |
| 32. | 40.56 |
| 33. | 35.84 |

The peptides of the invention are often administered in the form of pharmaceutically acceptable, nontoxic salts, such as acid addition salts, or of metal complexes, e.g., with zinc, barium, calcium, magnesium, aluminum or the like (which are considered as addition salts for purposes of this application), or of combinations of the two. Illustrative of such acid addition salts are hydrochloride, hydrobromide, sulphate, phosphate, nitrate, oxalate, fumarate, gluconate, tannate, maleate, acetate, citrate, benzoate, succinate, alginate, malate, ascorbate, tartrate and the like. For example, an aqueous solution of the peptide can be repeatedly treated with 1N acetic acid and then lyophilized to yield the acetic acid salt thereof. If the active ingredient is to be administered in tablet form, the tablet may contain a pharmaceutically-acceptable diluent which includes a binder, such as tragacanth, corn starch or gelatin; a disintegrating agent, such as alginic acid; and a lubricant, such as magnesium stearate. If administration in liquid form is desired, sweetening and/or flavoring may be used as part of the pharmaceutically-acceptable diluent, and intravenous administration in isotonic saline, phosphate buffer solutions or the like may be effected.

The pharmaceutical compositions will usually contain the peptide in conjunction with a conventional, pharmaceutically-acceptable carrier. Usually, the dosage will be from about 10 micrograms to about 2.5 milligrams of the peptide per kilogram of the body weight of the host when given intravenously; although oral dosages will be higher, it is anticipated that the nature of these compounds will permit effective oral administration. Overall, treatment of subjects with these peptides is generally carried out in the same manner as the clinical treatment using other antagonists or agonists of GnRH using a suitable carrier in which the peptide is soluble.

It may also be desirable to deliver the GnRH analog over prolonged periods of time, for example, for periods of one week to one year from a single administration, and slow release, depot or implant dosage forms may be utilized. For example, a dosage form may contain a pharmaceutically acceptable non-toxic salt of the compound which has a low degree of solubility in body fluids, for example, an acid addition salt with a polybasic acid; a salt with a polyvalent metal cation; or combination of the two salts. A relatively insoluble salt may also be formulated in a gel, for example, an aluminum stearate gel. A suitable, slow-release depot formulation for injection may also contain the GnRH analog or a salt thereof dispersed or encapsulated in a slow degrading, non-toxic or non-antigenic polymer such as a polylactic acid/polyglycolic acid polymer, for example, as described in U.S. Pat. No. 3,773,919. These compounds may also be formulated into silastic implants.

These peptides can be administered to mammals intravenously, subcutaneously, intramuscularly, orally, percutaneously, e.g. intranasally or intravaginally to achieve fertility inhibition and/or control and also in applications calling for reversible suppression of gonadal activity, such as for the management of precocious puberty or during radiation- or chemotherapy. They are also useful for treatment of steroid-dependent tumors. Effective dosages will vary with the form of administration and the particular species of mammal being treated. An example of one typical dosage form is a bacteriostatic water solution containing the peptide which solution is administered parenterally to provide a dose in the range of about 0.1 to 2.5 mg/kg of body weight per day. Oral administration of the peptide may be given in either solid form or liquid form.

Although the invention has been described with regard to its preferred embodiments, it should be understood that changes and modifications as would be obvious to one having the ordinary skill in this art may be made without departing from the scope of the invention which is set forth in the claims which are appended hereto. For example, other substitutions known in the art which do not significantly detract from the effectiveness of the peptides may be employed in the peptides of the invention. D-2PAL and D-4PAL are considered to be equivalents of D-3PAL. Instead of the amino group of Aph being situated at the para position, it may alternatively be located in the meta or ortho position. Other equivalent acylating groups can be used instead of acetyl at the N-terminus. The 6-position substitutes set forth in Table VI are considered to be equivalents known in the prior art and can be included in the peptides of the invention. Substituted Phe, such as (4F) Phe, can be used instead of Phe in the 7-position. Both butyl Lys and diethyl Lys are considered to be equivalents of ILys; however, ILys is preferred when neither U* or Arg is in the 8-position. Har is considered the equivalent of Arg in this position. Other hydrophobic amino acid residues can also be employed in the 1-position, preferably in D-isomer form, and are considered equivalents of those specified. Moreover, the analogs can be administered in the form of their pharmaceutically or vetinarially acceptable, nontoxic salts, as indicated hereinbefore, which are considered equivalents.

Particular features of the invention are emphasized in the claims which follow.

What is claimed is:

1. A method for making a peptide which includes at least one residue U* of an unnatural amino acid having the formula:

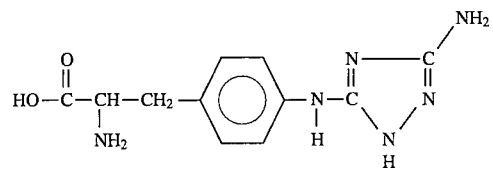

which peptide has the formula:

G-AA-AA$_2$-AA'-Ser-AA$_5$-AA$_6$-AA$_7$-AA$_8$-Pro-AA$_{10}$ wherein G is hydrogen or an acyl group having 7 or less carbon atoms; AA is AA$_1$ or pGlu; AA$_1$ is dehydroPro, D-pGlu, (A) D-Phe, (B)D-Trp, Pro, or β-D-NAL; A is H, Cl, F, NO$_2$, CH$_3$, OCH$_3$, C$^α$Me/4Cl, Cl$_2$ or Br; B is H, NO$_2$, NH$_2$, OCH$_3$, F, Cl, Br, CH$_3$, N$^{in}$For or N$^{in}$Ac; AA$_2$ is His or (A) D-Phe; AA' is AA$_3$ or Trp; AA$_3$ is U*, D-PAL, β-D-NAL or (B)D-Trp; AA$_5$ is U*, Lys(cpd), Orn(cpd), Dbu(cpd), Dpr(cpd), Tyr,(C)Arg, (A)Phe, (3I)Tyr or His; C is H or lower alkyl; AA$_6$ is U*, β-D-NAL, (B) D-Trp, (A')D-Phe, (D)D-Orn, (D)D-Lys, (D)Dbu, (D)D-Dpr, D-Har, D-Tyr, (E)D-His, D-PAL, (C)D-Arg, D-Leu, D-Ile, D-Nle, D-Val, D-Ala, or D-Ser(OtBu); A' is A, NH$_2$, NHCH$_3$ or gua; D is G, cpd or an aryl group; E is H, imBzl or dinitrophenol; AA$_7$ is Nle, Leu, NML, (A) Phe, Met, Nva, Tyr, (B)Trp or PAL; AA$_8$ is U*, ILys, (C')Arg or (C')Har; C' is H or di-lower alkyl; AA$_{10}$ is D-Ala-NH$_2$, Gly-NH$_2$, NHNH-CONH$_2$ or NH(R); R is lower alkyl; provided, however, that at least one of AA$_3$, AA$_5$, AA$_6$ and AA$_8$ is U*, which method comprises (a) forming an intermediate peptide having the formula:

X$^1$-AA-AA$_2$(X$^5$)-U$_3$-Ser (X$^3$)-U$_5$-U$_6$-AA$_7$ (X$^2$ or X$^7$)-U$_8$-Pro-X$^8$ wherein: U$_3$ is either U' or AA' (X$^2$); U$_5$ is either U' or AA$_5$(X$^4$ or X$^5$); U$_6$ is either U' or AA$_6$(X$^4$ or X$^5$ or X$^6$); U$_8$ is either U' or AA$_8$(X$^5$ or X$^6$); U' is Aph(X$^8$); X$^1$ is hydrogen or an α-amino protecting group; X$^2$ is hydrogen or a protecting group for an indole nitrogen; X$^3$ is a protecting group for a hydroxyl group of Ser or Thr; X$^4$ is hydrogen or a protecting group for a phenolic hydroxyl group of Tyr; X$^5$ is either hydrogen or a protecting group for a guanidino or imidazole group; X$^6$ is a protecting group for a primary amino group; X$^a$ is a protecting group for a primary amino group that is base-labile, hydrazine-labile or thio-labile; X$^7$ is hydrogen or a protecting group for Met; X$^8$ is Gly-NH-resin support, D-Ala-NH-resin support, N(A)-resin support, an amide either of Gly or of D-Ala or a substituted amide attached directly to Pro; provided however that at least one of U$_3$, U$_5$, U$_6$ and U$_8$ is Aph(X$^a$), with U$_3$ and U$_6$ always being a D-isomer; (b) removing at least one X$^a$ to selectively deprotect a side chain primary amino group of at least one Aph residue of said intermediate peptide; (c) reacting said deprotected Aph primary amino group to build said residue into one having the formula U* by first treating with diphenyl cyanocarbonimidate and subsequently treating with hydrazine to create amino-triazole moieties; and (d) splitting off any remaining groups X$^1$ to X$^7$ and/or cleaving from any resin support included in X$^8$.

2. A method in accordance with claim 1 wherein either U$_5$ is U' or U$_6$ is U' or both are U'.

3. A method in accordance with claim 1 wherein either U$_3$ or U$_8$ is U'.

4. A method in accordance with claim 1 wherein U$_5$ and U$_8$ are U'.

5. A method according to claim 1 for making a GnRH antagonist peptide having the formula: Ac-AA$_1$-(A)D-Phe- AA$_3$-Ser-AA$_5$-AA$_6$-AA$_7$-AA$_8$-Pro-AA$_{10}$ wherein AA$_1$ is (A)D-Phe, (B) D-Trp or β-D-2NAL; A is H, 4Cl, 4F, 4NO$_2$, 4CH$_3$, 4OCH$_3$, C$^α$Me/4Cl, 2,4Cl$_2$ or 4Br; B is H, 6NO$_2$, 6NH$_2$, 6OCH$_3$, 6F, 6Cl, 6Br, 6CH$_3$, N$^{im}$For or N$^{im}$Ac; AA$_3$ is U*, D-3PAL, β-D-2NAL or (B) D-Trp; AA$_5$ is U*, Lys(cpd) or Tyr; AA$_6$ is U*, β-D-2NAL, 4NH$_2$D-Phe, (B) D-Trp, D-Lys (cpd), D-3PAL or D-Arg; AA$_7$ is Nle, Leu, NML or Phe; AA$_8$ is U* ILys or Arg; provided, however, that at least one of AA$_3$, AA$_5$, AA$_6$ and AA$_8$ is U*, with AA$_3$ and AA$_6$ always being a D-isomer.

6. A method for making a GnRH antagonist peptide according to claim 5 wherein both AA$_5$ and AA$_6$ are U*.

7. A method for making a GnRH agonist peptide according to claim 1 wherein only AA$_6$ is U*.

8. A method according to claim 1 for making a GnRH antagonist peptide having the formula: Ac-AA$_1$-(A)D-Phe-AA$_3$-Ser-AA$_5$-AA$_6$-AA$_7$-AA$_8$-Pro-AA$_{10}$ wherein AA$_1$ is (A)D-Phe or β-D-2NAL; A is H, 4Cl, 1,4F, 4NO$_2$, 4CH$_3$, 4OCH$_3$, C$^α$Me/4Cl, 2,4Cl$_2$ or 4Br; AA$_3$ is D-3PAL, β-D-2NAL or (B) D-Trp; B is H, 6NO$_2$, 6NH$_2$, 6OCH$_3$, 6F, 6Cl, 6Br, 6CH$_3$, N$^{im}$For or N$^{im}$Ac; AA$_5$ is U*; AA$_6$ is U*, AA$_7$ is Nle, Leu, NML or Phe; and AA$_8$ is ILys or Arg; wherein Aph residues in AA$_5$ and AA$_6$ are simultaneously modified to create amino triazole moieties.

9. A method for making a peptide in accordance with claim 8 wherein AA$_1$ is β-D-2NAL, (A) is 4Cl or 4F and AA$_3$ is D-3PAL.

10. A method for making a peptide in accordance with claim 9 wherein AA$_8$ is ILys.

11. A method for making a GnRH antagonist peptide which includes at least one residue U* of an unnatural amino acid having the formula:

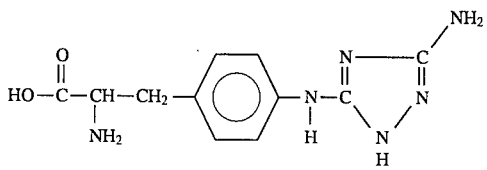

which peptide has the formula:

G-β-D-NAL- (A) D-Phe-D-PAL-Ser-AA$_5$-AA$_6$-Leu-AA$_8$-Pro-AA$_{10}$ wherein G is hydrogen or an acyl group having 7 or less carbon atoms; A is H, Cl, F, NO$_2$, CH$_3$, OCH$_3$, C$^α$Me/4Cl, Cl$_2$ or Br; AA$_5$ is U*; AA$_6$ is U*; AA$_8$ is ILys or Arg; AA$_{10}$ is D-Ala-NH$_2$, Gly-NH$_2$ or NHCH$_2$CH$_3$; with AA$_6$ being a D-isomer, which method comprises (a) forming an intermediate peptide having the formula: X$^1$-β-D-NAL- (A) D-Phe-D-PAL-Ser (X$^3$)-Aph (X$^a$)-D-Aph(X$^8$)-Leu-AA$_8$(X$^5$ or X$^6$)-Pro-X$^8$ wherein X$^1$ is hydrogen or an α-amino protecting group; X$^3$ is a protecting group for a hydroxyl group of Ser; X$^5$ is either hydrogen or a protecting group for a guanidino group; X$^6$ is a protecting group for an amino group; X$^a$ is a protecting group for a primary amino group that is base-labile, hydrazine-labile or thio-labile; X$^8$ is Gly-NH-resin support, D-Ala-NH-resin support or N(A)-resin support, (b) removing X$^a$ to deprotect side chain primary amino groups of said Aph residues of said intermediate peptide without removing other protecting groups; (c) reacting said deprotected side chain primary amino groups to simultaneously build each said Aph residue into one having the formula U* by first treating with diphenyl cyanocarbonimidate and subsequently treating with hydrazine to create amino-triazole moieties; and (d) splitting off any remaining groups X$^1$ to X$^6$ and cleaving from any resin support included in X$^8$.

12. A method according to claim 11 for making a GnRH antagonist peptide having the formula: Ac-β-D-2NAL-(A)D-phe-D-3pAL-Ser-AA$_5$-AA$_6$-Leu-AA$_8$-Pro-D-Ala-NH$_2$ wherein AA$_1$ is (A) D-Phe; A is 4Cl,4F or 4Br; AA$_5$ is Aph(tcg); AA$_6$ is D-Aph(tcg) and AA$_8$ is ILys or Arg.

13. A method for making a peptide in accordance with claim 12 wherein (A) is 4Cl or 4F.

14. A method for making a peptide in accordance with claim 13 wherein AA$_8$ is ILys.

15. A method for making a peptide in accordance with claim 12 wherein the decapeptide intermediate is formed and the N-terminus is deprotected and acetylated prior to removing X$^a$ as a part of step (b).

16. A method for making a peptide in accordance with claim 12 wherein X$^a$ is Fmoc and is removed with piperidine.

17. A method for making a peptide in accordance with claim 12 wherein said reaction with hydrazine is carried out in dimethylformamide at about 22° C.

18. A method for making a peptide in accordance with claim 11 having the formula:

Ac-β-D-2NAL-(4Cl)D-Phe-D-3PAL-Ser-Aph(3-amino 1,2,4 triazole)-D-Aph(3-amino 1,2,4 triazole)-Leu-Lys(isopropyl)-Pro-D-Ala-NH$_2$.

* * * * *

UNITED STATES PATENT AND TRADEMARK OFFICE
CERTIFICATE OF CORRECTION

PATENT NO : 5,580,957
DATED : December 3, 1996
INVENTOR(S): Hoeger, et al.

It is certified that error appears in the above-identified patent and that said Letters Patent is hereby corrected as shown below:

Column 31, line 17, Claim 8, change "4Cl, 1,4F," to --4Cl,4F,--. Column 32, line 24, Claim 12, change "3pAL" to --3PAL--.

Signed and Sealed this

Fifth Day of August, 1997

Attest:

BRUCE LEHMAN

*Attesting Officer*  *Commissioner of Patents and Trademarks*